US012201832B2

(12) United States Patent
Litvak et al.

(10) Patent No.: US 12,201,832 B2
(45) Date of Patent: Jan. 21, 2025

(54) STIMULATION THERAPY FOR TREATING OBSTRUCTIVE SLEEP APNEA (OSA) BASED ON COMPOUND MUSCLE ACTION POTENTIAL (CMAP)

(71) Applicant: Medtronic, Inc., Minneapolis, MN (US)

(72) Inventors: Leonid M. Litvak, Los Angeles, CA (US); Avram Scheiner, Vadnais Heights, MN (US); Kristin N. Hageman, Dayton, MN (US); Kanthaiah Koka, Valencia, CA (US); James Britton Hissong, Jacksonville, FL (US); Erik J. Peterson, Fridley, MN (US); David J. Miller, Austin, TX (US); Robert T. Sandgren, Lindstrom, MN (US); Adam J. Rivard, Blaine, MN (US); Sean P. Skubitz, Forest Lake, MN (US); Thomas I. Miller, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 438 days.

(21) Appl. No.: 17/656,586

(22) Filed: Mar. 25, 2022

(65) Prior Publication Data
US 2023/0302276 A1 Sep. 28, 2023

(51) Int. Cl.
*A61N 1/36* (2006.01)
*A61N 1/05* (2006.01)
*A61N 1/372* (2006.01)

(52) U.S. Cl.
CPC ....... *A61N 1/36003* (2013.01); *A61N 1/0548* (2013.01); *A61N 1/36139* (2013.01); *A61N 1/37235* (2013.01)

(58) Field of Classification Search
CPC .............. A61N 1/36003; A61N 1/0548; A61N 1/36139; A61N 1/37235; A61B 5/395; A61B 5/4818; A61B 5/682
See application file for complete search history.

(56) References Cited

U.S. PATENT DOCUMENTS 8,594,805 B2 11/2013 Ordonez et al.
9,757,560 B2* 9/2017 Papay .................. A61N 1/0551
(Continued)

FOREIGN PATENT DOCUMENTS

EP 3071288 B1 11/2018

OTHER PUBLICATIONS

International Search Report and Written Opinion of International Application No. PCT/IB2023/052943 dated Jun. 27, 2023, 11 pp.

*Primary Examiner* — Paula J Stice
(74) *Attorney, Agent, or Firm* — Shumaker & Sieffert, P.A.

(57) ABSTRACT

A medical system for obstructive sleep apnea (OSA) treatment includes therapy delivery circuitry configured to output one or more electrical stimulation signals to a tongue of a patient; sensing circuitry configured to sense one or more compound muscle action potential (CMAP) signals, wherein the one or more CMAP signals are generated in response to the delivery of the one or more electrical stimulation signals; and processing circuitry configured to: cause the therapy delivery circuitry to output the one or more electrical stimulation signals to the tongue; receive information indicative of the one or more CMAP signals from the sensing circuitry; determine, based on the one or more CMAP signals, one or more therapeutic stimulation parameters for the OSA treatment; and cause the therapy delivery
(Continued)

circuitry to deliver therapeutic electrical stimulation signals according to at least the determined one or more therapeutic stimulation parameters.

16 Claims, 10 Drawing Sheets

(56) References Cited

U.S. PATENT DOCUMENTS

| | | |
|---|---|---|
| 10,029,098 B2 | 7/2018 | Papay |
| 10,065,038 B2 | 9/2018 | Papay |
| 10,744,339 B2 | 8/2020 | Makansi |
| 2014/0243926 A1* | 8/2014 | Carcieri ............ A61N 1/36071 607/46 |
| 2020/0269044 A1 | 8/2020 | Papay |
| 2020/0282219 A1* | 9/2020 | Scheiner ............ A61N 1/36128 |
| 2020/0338358 A1 | 10/2020 | Makansi |
| 2020/0346017 A1 | 11/2020 | Caparso et al. |
| 2021/0228872 A1 | 7/2021 | Scheiner et al. |
| 2021/0290957 A1 | 9/2021 | Schulhauser et al. |

\* cited by examiner

STIMULATION THERAPY FOR TREATING OBSTRUCTIVE SLEEP APNEA (OSA) BASED ON COMPOUND MUSCLE ACTION POTENTIAL (CMAP)

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft pallet moving to the back of the throat and covering the airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to a medical device system and methods for therapy for obstructive sleep apnea (OSA) but can be extended to address other patient symptoms and disorders. With OSA, a patient's tongue may relax during sleep and block the patient's airway. Some example techniques to address OSA include electrically stimulating one or both hypoglossal nerves and/or motor points in the tongue of the patient. In response to the electrical stimulation, the hypoglossal nerve(s) causes protrusor muscles (e.g., genioglossus and geniohyoid muscles) to contract and move the tongue forward, thereby opening the airway. In some examples, in response to stimulating at the motor points of the protrusor muscles (e.g., a location where an axon of the hypoglossal nerve terminates at a muscle fiber), the protrusor muscles may contract to move the tongue forward, thereby opening the airway. Although the examples are described with respect to stimulation at motor points, the example techniques are not limited, and stimulation at other locations, such as along a trunk of the hypoglossal nerve is possible.

This disclosure describes example techniques of using compound muscle action potential (CMAP) signals as an example way in which to determine one or more therapeutic stimulation parameters of therapeutic stimulation signals. For example, processing circuitry may be configured to cause a therapy delivery circuitry to deliver one or more electrical stimulation signals, and receive information indicative of one or more CMAP signals generated in response to the one or more electrical stimulation signals. The processing circuitry may compare the CMAP signals (e.g., determine if there is a change in the CMAP signals, compare the CMAP signals to template, etc.), and determine the therapeutic stimulation parameters based on the electrical stimulation signal that caused the change in the CMAP signals.

In one example, the disclosure describes a medical system for obstructive sleep apnea (OSA) treatment, the system comprising: therapy delivery circuitry configured to output one or more electrical stimulation signals to a tongue of a patient via a first electrode configured to be implantable within the tongue; sensing circuitry configured to sense one or more compound muscle action potential (CMAP) signals via a second electrode configured to be implantable within the tongue, wherein the one or more CMAP signals are generated in response to the delivery of the one or more electrical stimulation signals; and processing circuitry configured to: cause the therapy delivery circuitry to output the one or more electrical stimulation signals to the tongue; receive information indicative of the one or more CMAP signals from the sensing circuitry; determine, based on the one or more CMAP signals, one or more therapeutic stimulation parameters for the OSA treatment; and cause the therapy delivery circuitry to deliver therapeutic electrical stimulation signals according to at least the determined one or more therapeutic stimulation parameters.

In one example, the disclosure describes a method of obstructive sleep apnea (OSA) treatment, the method comprising: causing, with processing circuitry, therapy delivery circuitry to output one or more electrical stimulation signals to a tongue of a patient via a first electrode configured to be implanted within the tongue; receiving, with the processing circuitry, information indicative of one or more compound muscle action potential (CMAP) signals from a sensing circuitry configured to sense the one or more CMAP signals via a second electrode configured to be implanted within the tongue, wherein the one or more CMAP signals are generated in response to the delivery of the one or more electrical stimulation signals; determining, with the processing circuitry and based on the one or more CMAP signals, one or more therapeutic stimulation parameters for the OSA treatment; and causing, with the processing circuitry, the therapy delivery circuitry to deliver therapeutic electrical stimulation signals according to at least the determined one or more therapeutic stimulation parameters.

In one example, the disclosure describes a computer-readable storage medium storing instructions thereon that when executed cause one or more processors to: cause therapy delivery circuitry to output one or more electrical stimulation signals to a tongue of a patient via a first electrode configured to be implanted within the tongue; receive information indicative of one or more compound muscle action potential (CMAP) signals from a sensing circuitry configured to sense the one or more CMAP signals via a second electrode configured to be implanted within the tongue, wherein the one or more CMAP signals are generated in response to the delivery of the one or more electrical stimulation signals; determine, based on the one or more CMAP signals, one or more therapeutic stimulation parameters for the OSA treatment; and cause the therapy delivery circuitry to deliver therapeutic electrical stimulation signals according to at least the determined one or more therapeutic stimulation parameters.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
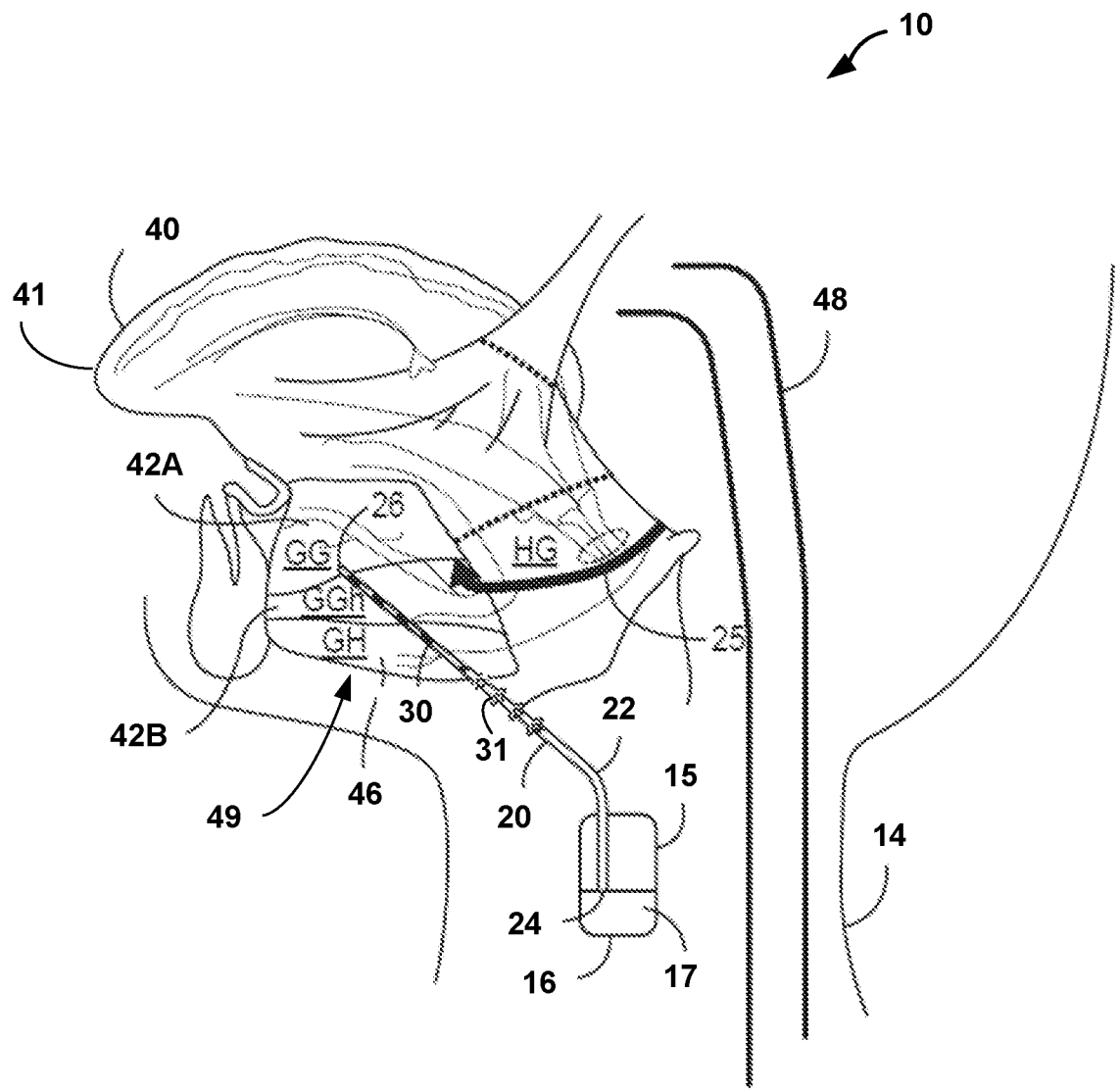
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue of a patient to enter an advanced state, during sleep, to avoid or reduce upper airway obstruction. As used herein, the term, "advanced state" with regard to the tongue refers to a position of the tongue that is moved forward and/or downward compared to a non-stimulated position or a relaxed position of the tongue. The advanced state is a state associated with contraction (e.g., via innervation from nerves in response to electrical stimulation) of protrusor muscles of the tongue (also sometimes referred to as "protruder" muscles of the tongue) including the genioglossus and geniohyoid muscles. An advanced state may be the opposite of a retracted and/or elevated position associated with the contraction of the retractor muscles (e.g., styloglossus and hyoglossus muscles) which retract and elevate the tongue. Alternatively, retracted state may indicate collapse of the tongue to the back of the airway; in this location, the tongue may block the airway. In that case, the advanced state indicates the state of the tongue away from the collapse state.

Electrical stimulation is delivered to cause the tongue to move (e.g., by depolarizing the nerve(s) that innervate the genioglossus and/or geniohyoid muscles) to and maintain the advanced state. As discussed above, the advanced state may prevent collapse or blockage of, open, or widen the upper airway of a patient to at least partially maintain or increase airflow (e.g., promote unrestricted airflow or at least reduced restriction of airflow during breathing).

A surgeon implants one or more leads that each include one or electrodes into the tongue such that the electrodes are proximate to a hypoglossal nerve and/or motor points (e.g., one or more locations where axons of the hypoglossal nerve terminate at respective muscle fibers of the protrusor muscles). For each of illustration, the example techniques are described with respect to stimulation near the motor points, but the example techniques are not so limited.

There are two hypoglossal nerves in the tongue of the patient. In one example, one lead may be used to stimulate (e.g., by delivering electrical stimulation through one or more electrodes of the lead) one of the two hypoglossal nerves, one lead may be used to stimulate both hypoglossal nerves, or two leads may be used, where each lead stimulates a respective one of the hypoglossal nerves. Stimulation of either or both hypoglossal nerves of the tongue can cause contraction of the protrusor muscles to reduce the effect of, or prevent, OSA.

There are multiple sets of motor points for each of the protrusor muscles on the left side and the right side. Each motor point may innervate one or more muscle fibers of the protrusor muscle. In one example, one lead may be used to stimulate motor points for the protrusor muscles on one side of the tongue, one lead may be used to stimulate motor points for protrusor muscles on both sides of the tongue, or two leads may be used, where each lead stimulates a respective set of motor points for the protrusor muscles on each side. Stimulation of either or both sets of motor points of the tongue can cause contraction of the protrusor muscles to reduce the effect of, or prevent, OSA.

This disclosure describes example techniques to determine the therapeutic electrical stimulation parameters for delivery of therapeutic electrical stimulation for OSA treatment. As one example, this disclosure describes example techniques of using compound muscle action potential (CMAP) signals for determining the therapeutic electrical stimulation parameters. CMAP signals are evoked, in that, CMAP signals are generated in muscles in response to (e.g., caused by) delivery of electrical stimulation.

A CMAP signal may be considered as including two components: an artifact component and non-artifact component (e.g., true CMAP signal component). In one or more examples, it may be possible to utilize both the artifact component and the non-artifact component of the CMAP signal for determining the therapeutic electrical stimulation parameters. In some examples, the example techniques may utilize the non-artifact component (e.g., subtract the artifact component from the sensed CMAP signal), and determine the therapeutic electrical stimulation parameters based on the non-artifact component.

Electromyography (EMG) signals may be considered as a different class of signals generated in muscles than CMAP signals. For instance, EMG signals may be intrinsic signals that are not evoked by delivery of electrical stimulation, and are present regardless of whether there is delivery of electrical stimulation.

The CMAP signals generated by muscles in a tongue of a patient may be indicative of the position of the tongue. Also, if the patient is receiving electrical stimulation signals that are therapeutic, there may be instances where the tongue experiences fatigue and there is a higher likelihood that the amplitude or energy of electrical stimulation signals is insufficient to provide effective therapy. In some cases, the CMAP signals may be indicative of tongue fatigue or voluntary movement of the tongue. In accordance with one or more examples described in this disclosure, processing circuitry may be configured to receive information indicative of one or more CMAP signals, and determine therapeutic stimulation parameters based on the one or more CMAP signals for OSA treatment.

In addition, changes in CMAP signals may be indicative of patient's posture. For example, if the patient is lying with their head facing the up, greater muscle activation may be required to move the tongue forward compared to patient lying on their side. If the patient is lying on their side, and then shifts their posture so that their head is facing up, and stimulation is not adjusted appropriately, tongue collapse may occur because the stimulation is insufficient to keep the tongue in the advanced state. Such tongue collapse may be indicated by changes in CMAP. The CMAP patterns may be differentiated between movement due to electrical stimulation or posture related movement.

In some examples, changes in the CMAP may occur due to tongue collapse (e.g., the tongue retracts and blocks airflow). In such examples, the airway may be obstructed in such a state (e.g., when the tongue retracts), which is undesirable, and when the tongue retracts, the CMAP signal may be indicative of this state.

In some examples, during the delivery of the electrical stimulation signals, the processing circuitry may receive CMAP signals. The processing circuitry may utilize the CMAP signals to control the delivery of the electrical stimulation signal based on changes observed due to fatigue or posture. For instance, the processing circuitry may update the therapeutic stimulation parameters, or cease delivery of the electrical stimulation signals (e.g., to allow the tongue to rest since keeping the tongue advanced may fatigue the tongue).

In this way, in one or more examples, rather than setting the therapy parameters (e.g., amplitude, frequency, pulse width, and/or which electrodes to use for stimulation) of the therapeutic stimulation signal to the maximum tolerable level, the example techniques utilize CMAP signals to determine the therapeutic stimulation parameters (e.g., amplitude, frequency, pulse width, and/or which electrodes to use for stimulation), which may promote efficient power usage. Also, because the CMAP signals may be used to control the delivery of the electrical stimulation signal, in some examples, the techniques provide for a closed-loop system to control whether electrical stimulation signals are delivered, and control the therapeutic stimulation parameters, which may result in more effective OSA treatment.

As an example, a medical device may be configured to deliver therapeutic electrical stimulation, and as the amplitude of the therapeutic electrical stimulation increases, at a particular amplitude, the tongue advances forward to open the airway. One example way to set the amplitude is during a clinical visit where a clinician can view the tongue and set the amplitude to a level based on amplitude that causes the tongue to advance opening the airflow. However, the amplitude of the electrical stimulation signal needed to ensure that the tongue advances may change from the amplitude set during the clinical visit for various reasons such as movement of the lead, changes in patient posture (e.g., changes in position of the head), or other reasons. Repeated clinical visits to readjust the parameters for effective electrical stimulation signals can be burdensome.

Another way to set the therapy parameters of the electrical stimulation signal is to set the therapy parameters to the maximum tolerable level to reduce the chances that the therapeutic electrical stimulation therapy is no longer therapeutic over time. In such cases, electrical stimulation signals at such therapy parameters, such as amplitude, may not be needed for therapeutic benefit, and can reduce the longevity of the medical device that provides the stimulation due to battery drain.

With the example techniques described in this disclosure, the processing circuitry may utilize CMAP signals for determining therapeutic electrical stimulation parameters. For instance, as described above, as the amplitude of an electrical stimulation signal is increased, at a certain amplitude, the tongue advances forward. The CMAP signal when the tongue is not in the advanced state (e.g., prior to the tongue moving forward) and the CMAP signal when the tongue moves to the advanced state (e.g., as the tongue is moving forward or after the tongue moves forward) is different (e.g., in terms amplitude, variance, etc.). The variance may be a measure of how much the tongue moves within a unit of time, or the first derivative of the tongue movement. That is, in some examples, the morphology of the CMAP signals may change as the tongue transitions to the advanced state. In one or more examples, the processing circuitry may utilize the change in the CMAP signals as a way to determine the amplitude of the electrical stimulation signal that provide therapeutic benefits.

For instance, on a periodic basis (e.g., nightly, weekly, etc.), the processing circuitry may sweep the amplitude of the electrical stimulation signal, and receive information indicative of the CMAP signals that are generated due to the delivery of the electrical stimulation signal. As another example, the processing circuitry may sweep the amplitude of electrical stimulation signal based on a determination of a change in patient posture. The processing circuitry may determine the amplitude of the electrical stimulation signal at which point there is a change the CMAP signals indicative of the tongue transitioning to an advanced state, or where the CMAP signals map to previously measured CMAP signals indicative of the tongue being in an advanced state. In this way, the processing circuitry may determine the amplitude of the electrical stimulation signal that provides therapeutic benefit in a closed-loop manner for OSA therapy.

As another example, the processing circuitry may use lower stimulation frequency (e.g., 1 to 2 Hz) that may not induce motion of the tongue. The processing circuitry may determine the CMAP signals generated in response to the stimulation having the lower frequency to determine a template of stimulation (e.g., determine inherent or baseline CMAP). The processing circuitry may sweep frequency, and deliver stimulation at a higher frequency (e.g., 40 Hz) to determine change in the CMAP signals. For instance, the processing circuitry may compare the CMAP signal generated at the higher frequency to the baseline CMAP signal, and determine if there is movement of the tongue.

In some examples, the processing circuitry may determine the minimum frequency that caused the tongue to move (e.g., as determined based on the CMAP signals) and use that frequency as the frequency for therapeutic stimulation. In some examples, the processing circuitry may also switch between different frequencies to help avoid fatigue.

The above provides some examples with respect to sweeping of amplitude and frequency. The example techniques described in this disclosure may also apply to sweeping pulse width.

Furthermore, after implantation, and during delivery of electrical stimulation signal, the tongue of the patient may fatigue. As the tongue fatigues, it may not immediately fall back and cover the airflow. Rather, the tongue may wobble. In one or more examples, the CMAP signals may change due to the wobbling. The processing circuitry may be configured to determine, based on the CMAP signals, whether the tongue is fatigued or fatiguing or due to posture changes. The processing circuitry may then adjust the amplitude to address the fatigue. For instance, the processing circuitry may temporally cease therapy to allow the tongue to rest, or increase the amplitude of the electrical stimulation signal to ensure that the tongue remains in the advanced state.

The above examples describe example techniques to utilize CMAP signals determine whether the tongue is moving, and determine therapy parameters accordingly. In some examples, additional parameters may be utilized for determining the therapy parameters. As one example, the posture of the patient may impact the amount of therapy that is needed to cause the tongue to advance. In one or more examples, the processing circuitry may be configured to receive information indicative of a patient posture (e.g., from an accelerometer, gyroscope, etc.). The processing circuitry may determine CMAP signals based on the patient posture. For instance, if there is a change in patient posture, the change in posture may trigger the processing circuitry to determine CMAP signals and change the therapy parameters in the event that the current therapy parameters are insufficient to ensure that the tongue remains in the advanced state (e.g., because different postures may require different amounts of therapy to cause tongue to be in the advanced state).

As another example, the processing circuitry may trigger determination of CMAP signals in response to a determination that the patient is sleeping. For instance, the processing circuitry may receive EEG signals, movement signals, respiration information, etc. to determine that the patient is sleeping. In response to determining that the patient is sleeping, the processing circuitry may trigger the determination of CMAP signals. However, it may be possible to determine the CMAP signals when the patient is awake as well.

The above examples are described with respect to amplitude, but the example techniques are not so limited. The processing circuitry may be configured to adjust one or more parameters of the electrical stimulation signal such as amplitude, pulse width, frequency, and which electrodes to use for stimulation based on the CMAP signals.

For instance, a system for OSA treatment includes therapy delivery circuitry configured to output one or more electrical stimulation signals to a tongue of a patient via a first electrode configured to be implantable within the tongue, and sensing circuitry configured to sense one or more compound muscle action potential (CMAP) signals via a second electrode configured to be implantable within the tongue. In some examples, the first electrode and the second electrode may be different electrodes, and in some examples, the first electrode and the second electrode may be the same electrodes. Also, in some examples, the electrodes used for sensing may be set or may be automatically adjusted. For instance, if artifacts versus non-artifacts portions are to be sensed, if large CMAP amplitude versus small CMAP amplitude is to be sensed, etc., then which electrodes are used for sensing may be automatically selected.

As described, the one or more CMAP signals are generated in response to the delivery of the one or more electrical stimulation signals. The system also includes processing circuitry that may be configured to cause the therapy delivery circuitry to output the one or more electrical stimulation signals to the tongue, receive information indicative of the one or more CMAP signals from the sensing circuitry, determine, based on the one or more CMAP signals, one or more therapeutic stimulation parameters for the OSA treatment, and cause the therapy delivery circuitry to deliver therapeutic electrical stimulation signals according to at least the determined one or more therapeutic stimulation parameters.

FIG. 1 is a conceptual diagram of a medical system for delivering OSA therapy. In system 10, implantable medical device (IMD) 16 and lead 20 are implanted in patient 14. IMD 16 includes housing 15 enclosing circuitry of IMD 16. In some examples, IMD 16 includes connector assembly 17, which is hermetically sealed to housing 15 and includes one or more connector bores for receiving a proximal end of at least one medical electrical lead 20 used for delivering OSA therapy. Although one lead 20 is illustrated in FIG. 1, there may be one or more leads 20 to which IMD 16 is coupled.

Lead 20 may include a flexible, elongated lead body 22, also called elongated member 22, that extends from lead proximal end 24 to lead distal end 26. As illustrated, lead 20 includes one or more electrodes 30 that are carried along a lead distal portion adjacent lead distal end 26 and are configured for insertion within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

As illustrated, distal end 26 of lead 20 includes one or more electrodes 30. Proximal end 24 of lead 20 includes one or more electrical contacts to connect to connector assembly 17. Lead 20 also includes conductors such as coils or wires that connect respective electrodes 30 to respective electrical contacts at proximal end 24 of lead 20.

While protrusor muscles 42 and 46 are described, the example techniques described in this disclosure are not limited to stimulating protrusor muscles 42 and 46. Also, FIG. 1 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 40 includes a second set of protrusor muscles.

In some examples, a surgeon may implant one or more leads 20 such that one or more electrodes 30 are implanted within soft tissue, such as musculature, proximate to medial branches of one or both hypoglossal nerves. In some examples, one or more electrodes 30 may be approximately 5 mm (e.g., 2 mm to 8 mm) from a major trunk of the hypoglossal nerve. In some examples, one or more electrodes 30 may be placed in an area of protrusor muscles 42 and 46 that include motor points, where each nerve axon terminates in the muscle (also called the neuro-muscular junction). The motor points are not at one location but spread out in the protursor muscles. Leads 20 may be implanted such that one or more electrodes 30 may be generally in the area of the motor points (e.g., such that the motor points are within 1 to 10 mm from one or more electrodes 30).

Tongue 40 includes a distal end (e.g., tip of tongue 40), and electrodes 30 may be implanted proximate to root 49 of tongue 40. The surgeon may implant one or more leads 20 such that one or more electrodes are implanted proximate to root 49 of tongue 40, as illustrated in FIG. 1. For example, the location for stimulation for the genioglossus muscle 42 may be approximately 30 mm (e.g., 25 mm to 35 mm) from the symphysis of the jaw (e.g., where the genioglossus and hypoglossal muscles insert). The location for stimulation for the geniohyoid muscle 46 may be approximately 40 mm (e.g., 35 mm to 45 mm) from the symphysis. For both the genioglossus muscle 42 and the geniohyoid muscle 44, the location for stimulation may be approximately 11 mm (e.g., 7 mm to 15 mm) lateral to the midline on both the right and left sides of tongue 40 for stimulating respective hypoglossal nerves. In some examples, rather than stimulating hypoglossal nerves, the examples described in this disclosure may be configured for stimulating the motor points. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

One or more electrodes 30 of lead 20 may be ring electrodes, segmented electrodes, partial ring electrodes or any suitable electrode configuration. Ring electrodes extend 360 degrees around the circumference of the lead body of lead 20. Segmented and partial ring electrodes each extend along an arc less than 360 degrees (e.g., 90-120 degrees) around the outer circumference of the lead body of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 20 may be, at least in part, paddle-shaped (e.g., a "paddle" lead), and may include an array of electrodes arranged as contacts or pads on a common surface, which may or may not be substantially flat and planar.

As described above, in some examples, electrodes 30 are within musculature of tongue 40. Accordingly, one or more electrodes 30 may be "intramuscular electrodes." Intramuscular electrodes may be different than other electrodes that are placed on or along a nerve trunk or branch, such as a cuff electrode, used to directly stimulate the nerve trunk or branch. The cuff, with the cuff electrodes, includes the cuff electrodes on one side of the cuff (e.g., the side that wraps around the nerve). In one or more examples, the other side of the cuff may include one or more electrodes configured to sense the EMG signals and/or CMAP signals. In some examples, the side of the cuff that includes the electrodes for stimulation may also include one or more electrodes for sensing EMG signals and/or CMAP signals. The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve.

In some examples, lead 20 may be configured for advancement through the soft tissue, which may include the protrusor muscle tissue, to anchor electrodes 30 in proximity to the hypoglossal nerve(s) that innervate protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, for instance, to promote a reduction in obstruction or narrowing of the upper airway 48 during sleep. As used herein, the term "activated" with regard to the electrical stimulation of protrusor muscles 42 and 46 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40 (e.g., the left or right side of tongue 40), may be activated by a medial branch of a first hypoglossal nerve, and the protrusor muscles, on a second side of tongue 40 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g. such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

Figure 2:
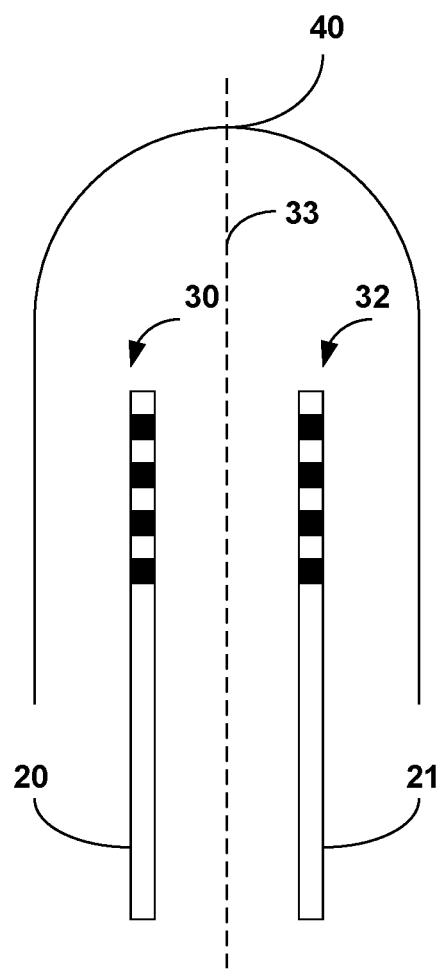
FIG. 2 is a conceptual diagram illustrating example location of lead implantation and sensing of compound muscle action potential (CMAP) signals.

In some examples, one lead 20 may be implanted such that one or more of electrodes 30 deliver electrical stimulation to stimulate the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the right side of tongue and cause the right protrusor muscles to activate. In some examples, one lead 20 may be implanted such that one or more of electrodes 30 deliver electrical stimulation to stimulate the right hypoglossal nerve or motor points of protrusor muscles on the right side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate. Accordingly, in some examples, two leads like lead 20 may be implanted to stimulate each of the left and right hypoglossal nerves and/or motor points of respective protrusor muscles on the left and right side of tongue 40. An example of the two leads being implanted for stimulating the left and right side of tongue 40 is illustrated in FIG. 2.

In some examples, one lead 20 may be implanted substantially in the middle (e.g., center) of tongue 40. In such examples, one or more electrodes 30 may deliver electrical stimulation to both hypoglossal nerves or motor points of both muscles on both sides of tongue 40, causing both hypoglossal nerves or motor points to activate respective left and right protrusor muscles. It may be possible to utilize current steering and field shaping techniques such that one or more electrodes 30 deliver first electrical stimulation that stimulates the left hypoglossal nerve or motor points of protrusor muscles on the left side of tongue 40 with little to no stimulation of the right hypoglossal nerve or motor points of protrusor muscles on the right side of tongue 40, and then one or more electrodes 30 deliver second electrical stimulation that stimulates the right hypoglossal nerve or motor points of protrusor muscles on the right side of tongue with little to no stimulation of the left hypoglossal nerve or motor points of protrusor muscles on the left side of tongue. In examples where two leads like lead 20 are utilized, each lead may alternate delivery of stimulation to respective hypoglossal nerves or motor points. In this way, IMD 16 may stimulate one hypoglossal nerve or one set of motor points and then the other hypoglossal nerve or another set of motor points, which can reduce muscle fatigue.

For instance, continuous stimulation may cause protrusor muscles to be continuously in an advanced state. This continuous contraction may cause protrusor muscles 42 and/or 46 to fatigue. In such cases, due to fatigue, the stimulation may not cause protrusor muscles 42 and/or 46 to maintain an advanced state (or higher intensity of the electrical stimulation may be needed to cause protrusor muscles 42 and/or 46 to remain in the advanced state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 can remain in the advanced state, while one of the first or second set of protrusor muscles is at rest.

In some examples, one lead 20 may be implanted laterally or diagonally across tongue 40 such that some of electrodes 30 on lead 20 can be used to stimulate the left hypoglossal nerve and/or motor points of the protrusor muscles on the left side of tongue 40 and some of electrodes 30 on the same lead 20 can be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on a first side of tongue 40 via a first set of one or more electrodes 30, and then deliver electrical stimulation to a second hypoglossal nerve and/or/or second set of motor points of the protrusor muscles on a second side of tongue 40 via a second set of one or more electrodes 30. This may be another way in which to reduce muscle fatigue.

Lead proximal end 24 includes a connector (not shown in FIG. 1) that may be coupled to connector assembly 17 of IMD 16 to provide electrical connection between circuitry enclosed by the housing 15 of IMD 16. Lead body 22 encloses electrical conductors extending from each of one or more electrodes 30 to the proximal connector at proximal end 24 to provide electrical connection between output circuitry of IMD 16 and the electrodes 30.

FIG. 1 illustrates the location of IMD 16 as being within or proximate to the neck of patient 14. However, IMD 16 may be implanted in various other locations. As one example, the surgeon may implant IMD 16 in the left or right pectoral region. For instance, the surgeon may plan on implanting IMD 16 in the left pectoral region unless another medical device is already implanted in the left pectoral region. If another medical device is already implanted in the left pectoral region, the surgeon may then implant IMD 16 in the right pectoral region. There may other locations where the surgeon may implant IMD 16 such as the back of patient 14, and other locations in the head such as below and behind an ear, or in the chin, etc. The example techniques are not limited to any particular implant location of IMD 16.

This disclosure describes example ways in which to determine, in a closed-loop manner, therapeutic stimulation parameters so that IMD 16 can deliver therapeutic stimulation signals that treat OSA. For instance, the protrusor muscles of tongue 40 may generate a compound muscle action potential (CMAP) signal in response to IMD 16 delivering an electrical stimulation signal. The CMAP signal is an evoked signal, where the electrical stimulation signal causes the CMAP signal to be generated.

In one or more examples, the CMAP signals may be indicative of the state of tongue 40, such as whether tongue 40 is in an advanced state or whether tongue 40 is fatiguing, or generally whether there is movement in tongue 40, such as from change in posture. Processing circuitry (e.g., processing circuitry of IMD 16, some other processing circuitry, or a combination of processing circuitry) may be configured to utilize one or more CMAP signals for determining the therapeutic stimulation parameters for the therapeutic electrical stimulation signals that IMD 16 is to deliver.

For instance, the therapeutic stimulation parameters, such as amplitude, pulse width, frequency and/or which electrodes to use for stimulation, may need to be periodically updated or adjusted for various reasons. As one example, a clinician may have set the therapeutic stimulation parameters after implant of lead 20. However, over time lead 20 may migrate and the therapeutic stimulation parameters may need to be adjusted due to lead migration, posture change, changes in disease state, etc. There may be other causes for needing to periodically update or adjust therapeutic stimulation parameters, and lead migration is one example cause.

Accordingly, the processing circuitry may periodically determine the therapeutic stimulation parameters in a closed-loop manner to ensure that the therapeutic stimulation parameters are at the correct level to provide efficacious therapy. Examples of periodically determining the therapeutic stimulation parameters may refer determining the therapeutic stimulation parameters daily, weekly, monthly, etc.

Additional examples of periodically determining the therapeutic stimulation parameters includes a determination of a change in a sleeping position or a determination that the patient is sleeping. For example, an accelerometer, gyroscope, etc. within IMD 16 may determine a posture of the patient. The amount of therapy (e.g., amplitude, pulse width, frequency, and/or which electrodes are used) needed may be factor of posture. In one or more examples, if there is a change in posture, IMD 16 may determine CMAP signals to determine if changes to therapy parameters is appropriate. Also, in some examples, IMD 16 may determine CMAP signals when the patient is sleeping (e.g., as determined based on EEG signals, movement information, respiration information, etc.). However, IMD 16 may determine the CMAP signals when the patient is awake in some examples.

Periodically determining the therapeutic stimulation parameters may also refer to examples where the patient or clinician requests determining the therapeutic stimulation parameters. Determining the therapeutic stimulation parameters in a closed-loop manner may refer to the processing circuitry determining the therapeutic stimulation parameters based on sensed signals (e.g., CMAP signals) such as where the sensed signals form a feedback that the processing circuitry can use to adjust parameters.

For treating OSA, tongue 40 should be an advanced state to open airflow. The CMAP signals that the protrusor muscles generate in response to delivery of electrical stimulation signal may be different based on whether the tongue is in a non-advanced state or in the advanced state. In one or more examples, the processing circuitry may cause IMD 16 to output a plurality of electrical stimulation signals having different energy (e.g., having different amplitudes). The processing circuitry may start from a low amplitude electrical stimulation signal and sweep to a high amplitude electrical stimulation signal. For each of the plurality of electrical stimulation signal, the processing circuitry of the IMD may receive a correspond CMAP signal that is generated in response to the delivery of the electrical stimulation signal. In this way, there may be a plurality of CMAP signals.

During the sweep of the amplitude, at a certain amplitude of the electrical stimulation signal, tongue 40 may advance sufficiently to open the airflow. In one or more examples, when tongue 40 moves to the advanced state, the CMAP signal may change. Examples of changes in the CMAP signal may include a change in one or more of an amplitude between the two or more of the plurality of CMAP signals, a shape between the two or more of the plurality of CMAP signals, and whether there is a change in a variance between the two or more of the plurality of CMAP signals.

As another example, the processing circuitry may use lower stimulation frequency (e.g., 1 to 2 Hz) that may not induce motion of the tongue. The processing circuitry may determine the CMAP signals generated in response to the stimulation having the lower frequency to determine a template of stimulation (e.g., determine inherent or baseline CMAP). The processing circuitry may sweep frequency, and deliver stimulation at a higher frequency (e.g., 40 Hz) to determine change in the CMAP signals. For instance, the processing circuitry may compare the CMAP signal generated at the higher frequency to the baseline CMAP signal, and determine if there is movement of tongue 40.

In some examples, the processing circuitry may determine the minimum frequency that caused tongue 40 to move (e.g., as determined based on the CMAP signals) and use that frequency as the frequency for therapeutic stimulation. In some examples, the processing circuitry may also switch between different frequencies to help avoid fatigue.

The processing circuitry may perform similar operations with pulse width. In some examples, the processing circuitry may sweep amplitude, frequency, and pulse width together to simultaneously identify the amplitude, frequency, and pulse width at which there is change in the CMAP signals. The processing circuitry may determine the amplitude, frequency, and pulse width of the therapeutic electrical stimulation signals according to at least the amplitude, frequency, and pulse width that together caused the change in the CMAP signals.

The CMAP signals may be considered as including an artifact portion and a non-artifact portion. The artifact portion may be located in initial portion of the CMAP signals (e.g., such as in the first 3 milliseconds). The artifact portion may represent a sharp increase and decrease in amplitude. In some examples, the artifact portion may correspond to direct detection or representation of a bi-phasic stimulation pulse delivered to the patient that elicits the CMAP to follow. For instance, content in the CMAP signals having relative high frequency and amplitude as compared to other content in the CMAP signals may be the artifact portion of the CMAP signals. The non-artifact portion of the CMAP signals may start after the artifact portion, and may be generally include lower frequency content with lower amplitudes.

In one or more examples, to determine the change in CMAP signals, the processing circuitry may be configured to determine if there is a change in both the artifact portion and the non-artifact portion of the one or more CMAP signals. In another example, the processing circuitry may determine if there is a change in the non-artifact portion of the one or more CMAP signals, and a change in the artifact portion may be immaterial, or a change in artifact portion of the one or more CMAP signals, and a change in the non-artifact portion may be immaterial. That is, to determine the one or more therapeutic stimulation parameters, the processing circuitry may be configured to determine the one or more therapeutic stimulation parameters based on both the artifact portion and the non-artifact portion of the one or more CMAP signals, the non-artifact portion of the one or more CMAP signals, and not the artifact portion, or the artifact portion of the one or more CMAP signals, and not the non-artifact portion.

As an example, the processing circuitry may subtract the artifact portion from the one or more CMAP signals to determine the non-artifact portion (e.g., to have the true CMAP signal). The processing circuitry may determine if there is change in the non-artifact portion to determine therapeutic electrical stimulation parameters. As another example, changes in the artifact portion may be indicative of movement of tongue 40. For instance, if there is no movement, the artifact portion should increase linearly with increase in stimulation. However, if there is a non-linear change in the artifact portion, such non-linear change may be indicative of movement of tongue 40. Accordingly, in one or more examples, both changes in the non-artifact and artifact portions of the CMAP signals may be indicative of tongue movement, and the processing circuitry may utilize both the artifact and non-artifact portions of the CMAP signals to determine therapeutic electrical stimulation parameters, only the non-artifact portion of the CMAP signals to determine therapeutic electrical stimulation parameters, or only the artifact portion of the CMAP signals to determine therapeutic electrical stimulation parameters.

The processing circuitry may determine, based on the one or more CMAP signals, one or more therapeutic stimulation parameters for the OSA treatment. For example, the processing circuitry may determine the parameters of the electrical stimulation signal at which point there was a change in the CMAP (e.g., change in the artifact portion, non-artifact portion, or both). For instance, the processing circuitry may determine the amplitude, pulse width, frequency, and/or which electrodes were used for stimulation of the electrical stimulation signal that caused there to be a change in the CMAP signal.

As an example, the processing circuitry may be configured to compare two or more of the plurality of CMAP signals to each other (e.g., to one another). To determine the one or more therapeutic stimulation parameters based on the one or more CMAP signals for OSA treatment, the processing circuitry may be configured to determine the one or more therapeutic stimulation parameters based on the comparison. For instance, the processing circuitry may determine for which one of the two or more of the plurality of CMAP signals there is a change relative to another one of the two or more of the plurality of CMAP signals. In some examples, if there is no change in the CMAP signals, but a change was expected, the processing circuitry may keep changing the parameters until there is a change in CMAP signals, as a lack of change in CMAP signals may be indicative of a desire to change therapy parameters. The processing circuitry may determine an electrical stimulation signal of the plurality of electrical stimulation parameters that generated the determined one of the plurality of CMAP signals, determine one or more stimulation parameters for the determined electrical stimulation signal, and determine the one or more therapeutic stimulation parameters based on the determined one or more stimulation parameters.

As an example, if the amplitude of the electrical stimulation signal that caused the change in the CMAP signal is X mA, then the processing circuitry may set the amplitude of the therapeutic electrical stimulation signal to X mA. In this case, X mA may be the minimal amplitude needed to ensure that tongue 40 is in the advanced state. By delivering therapeutic electrical stimulation signals at X mA, the example techniques may ensure that the patient receives OSA treatment, while preserving power. Moreover, if a change in therapy is needed, the example techniques may re-determine the therapeutic stimulation parameters in a way that identifies the therapeutic stimulation parameter that preserves power without requiring the patient to visit a clinic.

As another example, the processing circuitry may utilize a lack of change in the CMAP to infer that there is no motion of tongue 40 (e.g., there is possible of tongue collapse). For instance, after determining the therapeutic stimulation parameters, and sweeping from low energy to the energy level consistent with the determined therapeutic stimulation parameters, if there is no change in the CMAP signal, there is a possibility of tongue collapse (e.g., due to fatigue or other causes). In such examples, the processing circuitry may initiate full-strength therapy (e.g., higher amplitude, frequency, and/or pulse width than was previously determined) or rescue therapy.

In one or more examples, the processing circuitry may determine, based on the one or more CMAP signals, one or more therapeutic stimulation parameters for the OSA treatment. As another example, the processing circuitry may utilize CMAP signals to determine cross-innervation. For instance, there can be cross-innervation with some nerves innervating different parts of tongue 40.

The processing circuitry may be configured to identify pairs of electrodes which stimulation non-overlapping parts of tongue 40. For example, the processing circuitry may stimulate a first side of tongue 40 to evoke a first CMAP signal in the first side of tongue 40. The processing circuitry may receive information indicative of the first CMAP signal. The processing circuitry may stimulate a second side of tongue 40 to evoke a second CMAP signal in the second side of tongue 40. The processing circuitry may receive information indicative of the second CMAP signal.

The processing circuitry may together both the first and second sides of tongue 40 (e.g., simultaneously stimulate) to evoke a combined CMAP signal in tongue 40. The processing circuitry may receive information indicative of the combined CMAP signal.

In one or more examples, the processing circuitry may add the first CMAP signal and the second CMAP signal to generate a summed CMAP signal. The processing circuitry may compare the summed CMAP signal to the combined CMAP signal. If the summed CMAP signal is substantially equal (e.g., within 10%) to the combined CMAP signal, there may not be cross-innervation (e.g., stimulation provided on the first side is not causing a CMAP on the second side, and vice-versa). If the summed CMAP signal is not equal to the combined CMAP signal, there may be cross-innervation (e.g., stimulation on the first side is causing a CMAP on the second side, or vice-versa).

In one or more examples, the processing circuitry may determine one or more therapeutic stimulation parameters for the OSA treatment based on the first CMAP signal, the second CMAP signal, and the combined CMAP signal. For instance, the processing circuitry may adjust the pulse width, frequency, amplitude, and/or which electrodes to use for stimulation to achieve cross-innervation or decrease cross-innervation. In some examples, the processing circuitry may also control duty cycle between the first side and the second side of tongue 40 (e.g., the amount of time that each side is stimulated) to achieve cross-innervation or decrease cross-innervation.

As one example, the processing circuitry may determine therapeutic electrical stimulation parameters that reduce cross-innervation, higher strength signals may provide cross-innervation, but lower strength signals may not. Hence, for power savings, there may be benefit of reducing cross-innervation. Also, the processing circuitry may determine therapeutic electrical stimulation parameters that reduce cross-innervation to reduce fatigue. For instance, if there is cross-innervation, then both the first and second sides of tongue 40 may move in response to stimulation. However, if there is not cross-innervation, then when stimulation is applied to the first side of tongue 40, the second side of tongue 40 can rest.

There may be instances where increasing cross-innervation is useful. As one example, for tongue collapse, it may be beneficial to provide sufficient therapeutic electrical stimulation to innervate both the first and second sides of tongue 40 to ensure that tongue 40 advances forward.

The above examples are described with respect to stimulate the first side and the second side of tongue 40, but the example techniques are not so limited. In some examples, the processing circuitry may be configured to determine innervation across the same side. For instance, lead 20 is a multi-contact lead (e.g., having a plurality of electrodes 30). The processing circuitry may determine a first CMAP signal evoked from stimulation delivered to a first one of electrode 30, determine a second CMAP signal evoked from stimulation delivered to a second one of electrode 30, and so forth. The processing circuitry may evoke a combined CMAP signal by stimulating on all electrodes 30. The processing circuitry may sum the first, second, and so forth CMAP signals evoked from stimulating across each of electrodes 30. The processing circuitry may compare the summed CMAP signal to the combined CMAP signal for determining the innervation. The processing circuitry may adjust the therapeutic electrical stimulation parameters to achieve innervation or decrease innervation as needed.

FIG. 2 is a conceptual diagram illustrating example location of lead implantation and sensing of compound muscle action potential (CMAP) signals. For instance, FIG. 2 illustrates lead 20 and lead 21 implanted in tongue 40 near motor points (e.g., a location where an axon of the hypoglossal nerve terminates at a muscle fiber) of the protrusor muscles 42 and/or 46 on each side of medial line 33. That is, lead 20 may be considered as stimulating motor points near the left hypoglossal nerve, and lead 21 may be considered as stimulating motor points near the right hypoglossal nerve.

As illustrated, lead 20 includes one or more electrodes 30, and lead 21 includes one or more leads 32. To deliver therapeutic electrical stimulation, in one or more examples, IMD 16 may be configured to deliver a therapeutic electrical stimulation signal through one or more of electrodes 30 to stimulate the left part of tongue 40 to activate the protrusor muscles on the left side of tongue 40, and advance tongue 40. Then, IMD 16 may be configured to deliver a therapeutic electrical stimulation signal through one or more of electrodes 30 to stimulate the right part of tongue 40 to activate the protrusor muscles on the right side of tongue 40, and advance tongue 40. In this example, IMD 16 may alternate delivery of therapy between left and right sides of tongue 40, which causes tongue 40 to advance, while minimizing fatigue. In some examples, IMD 16 may alternate between different sets of electrodes on the same side of tongue 40.

In accordance with examples described in this disclosure, the processing circuitry may be configured to utilize CMAP signals to determine if adjustment to therapy parameters is appropriate. In some examples, the CMAP signals may be indicative of whether tongue 40 is fatiguing. In one or more examples, if the processing circuitry determines that a first side of tongue 40 is fatiguing, the processing circuitry may cause delivery of electrical stimulation to the second side of tongue 40 for longer time to allow the first side to rest.

For example, if one side of tongue 40 is the only side that is stimulated, the protrusor muscles on that side of tongue 40 may fatigue, and more and more energy may be needed in the electrical stimulation signal to cause tongue 40 to advance. By alternating stimulation, when one side of tongue 40 is being stimulated, the other side is at rest, and vice-versa, which can reduce fatigue.

In some examples, the amplitude of the therapeutic electrical stimulation signal may be ramped up to the desired level on a first side of tongue 40, while the amplitude of the therapeutic electrical stimulation signal may be ramped down on a second side of tongue 40. In this manner, the total amplitude of the electrical stimulation signal may be generally constant.

The example techniques are described with bilateral stimulation (e.g., alternating stimulation), but the example techniques are not so limited. In some examples, a single lead may be implanted in tongue 40. In such examples, the same set of electrodes may be used to deliver therapeutic electrical stimulation signals, or the electrodes that deliver the therapeutic electrical stimulation signals may be cycled (e.g., rotated across implanted electrode pairs).

In accordance with one or more examples described in this disclosure, IMD 16 may output one or more electrical stimulation signals to tongue 30 via a first electrode (e.g., one of electrodes 30) configured to be implantable within tongue 40. IMD 16 may sense one or more CMAP via a second electrode (e.g., one of electrodes 31) configured to be implantable within tongue 40. However, in some examples, the first electrode and the second electrode may be the same electrode (e.g., the same one of electrodes 30) or same electrodes on the same lead (e.g., one of electrodes 30 for stimulation and another one of electrodes 30 for sensing). Also, in some examples, the electrodes used for sensing may be set or may be automatically adjusted. For instance, if artifacts versus non-artifacts portions are to be sensed, if large CMAP amplitude versus small CMAP amplitude is to be sensed, etc., then which electrodes are used for sensing may be automatically selected. As described, the one or more CMAP signals are generated in response to the delivery of the one or more electrical stimulation signals.

For instance, the electrodes the perform the sensing (e.g., one of electrodes 31) may be different than the electrodes that delivered the stimulation (e.g., one of electrodes 30). In some examples, it may be possible to rotate the pairs of electrodes that are used for sensing. Also, in some examples, such as the example described above, the sensing electrodes (e.g., one of electrodes 31) may be on a different lead than lead 20 that includes the stimulation electrodes (e.g., one of electrodes 30). However, the example techniques are not so limited, in some examples, it may be possible for the stimulation electrodes and the sensing electrodes to be on the same lead.

In the above example, one of electrodes 30 is described as being the stimulation electrode, and one of electrodes 31 is described as being the sensing electrode. In accordance with one or more examples, after using one of electrodes 30 for stimulation, and one of electrodes 31 for sensing, IMD 16 may alternate, and use one of electrodes 31 for stimulation, and one of electrodes 30 for sensing. In this way, when there is a stimulation signal using electrodes on a first lead, the electrodes on the second lead may be used for sensing the CMAP signal. For instance, the delivery of an electrical stimulation signal using electrodes on the first lead may generate a CMAP signal that is sensed using electrodes on the second lead. In accordance with one or more examples, IMD 16 may record the CMAP signals generated from the bilateral stimulation, and IMD 16 may determine therapeutic electrical stimulation parameters based on the CMAP signals, such as based on changes in the CMAP signals.

Both recordings on the same lead and different lead may have individual advantages. For example, recordings on the same lead may be most indicative of threshold to stimulation (stimulation which just evokes minimal activation of the tongue musculature) while CMAPs recorded on a different lead may be indicative of global activation of the tongue and therefore better correlated to tongue reaching a therapeutic level.

Figure 3:
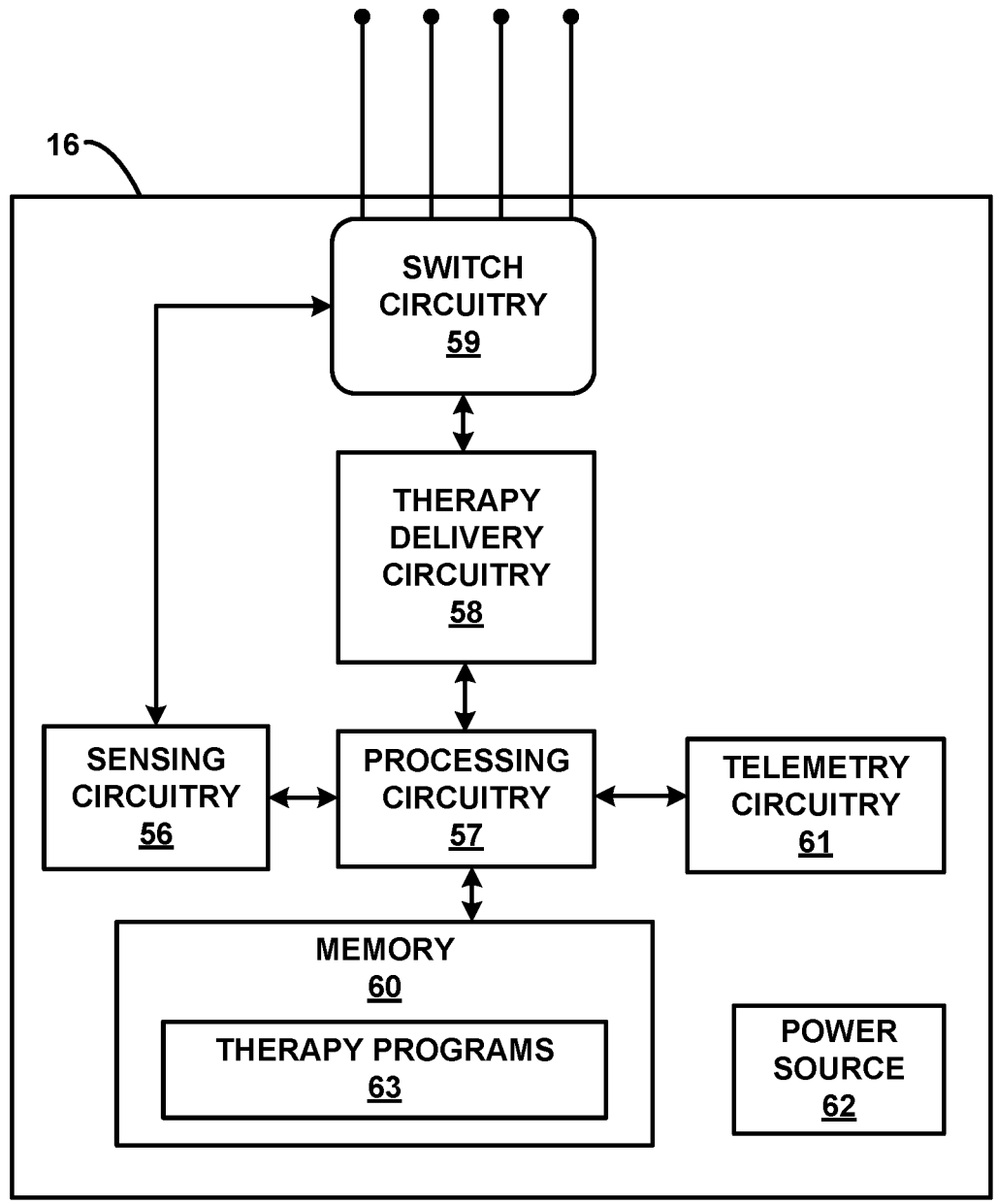
FIG. 3 is a block diagram illustrating example configurations of implantable medical devices (IMDs) which may be utilized in the system of FIG. 1.

FIG. 3 is block diagram illustrating example configurations of implantable medical devices (IMDs) which may be utilized in the system of FIG. 1. As shown in FIG. 3, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components.

Switch circuitry 59 may be configured to, in response to instructions from processing circuitry 57, switch the coupling of electrodes 30 between sensing circuitry 56 and therapy delivery circuitry 58. For instance, switch circuitry 59 may be configured to allow therapy delivery circuitry 58 to deliver electrical stimulation signal via one or more electrodes 30 of lead 20, and allow sensing circuitry 56 to sense the CMAP signal from one or more electrodes 31 of lead 22 that are generated in response to the delivery of the electrical stimulation signal. In this example, switch circuitry 59 may couple therapy delivery circuitry 58 to one or more electrodes 30 of lead 20, and couple sensing circuitry 56 to one or more electrodes 31 of lead 22. After sensing circuitry 56 senses the CMAP signal, switch circuitry 59 may couple therapy delivery circuitry 58 to one or more electrodes 31 of lead 22, and couple sensing circuitry 56 to one or more electrodes 30 of lead 20. Switch circuitry 59 may repeat such operations.

In some examples, therapy delivery circuitry 58 may include a plurality of regulated current sources or sinks, with each current source or sink coupled to one of electrodes 30 or 31. In such examples, therapy delivery circuitry 58 may control each current source or sink and switching between electrodes 30 and 31 may not be necessary for therapy delivery since each one of electrodes 30 and 31 is individually controllable.

Although not shown in FIG. 3, in some examples, IMD 16 may include one or more sensors configured to sense posture or position of patient 14. For example, IMD 16 may include accelerometer to determine if patient 14 is lying down, whether lying on a back, whether lying on a side, and generally posture of patient 14. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuitry 57 may control delivery of therapy based on information received from the one or more sensors, such as delivery of therapy after sensing an onset of OSA.

In some examples, electrodes 30 and 31 may be configured to sense electromyogram (EMG) signals in addition to CMAP signals. Sensing circuitry 56 may be coupled to electrodes 30 and 31 via switch circuitry 59 to be used as EMG or CMAP sensing electrodes when electrodes 30 and 31 are not being used for stimulation. EMG signals may be used by processing circuitry 57 to detect sleep state and/or low tonal state of protrusor muscles 42 and/or 46 for use in delivering electrical stimulation. In some examples, the EMG signal may also indicate posture of patient 14. In some examples, rather than using electrodes 30 or in addition to using electrodes 30, there may be other electrodes or sensors used to sense EMG signals.

In accordance with one or more examples described in this disclosure, in addition to or instead of relying upon EMG signals to detect tonal state of protrusor muscles 42 and/or 46, processing circuitry 57 may utilize CMAP signals to detect tonal state. As described, CMAP signals may be a class of signals that are evoked due to the delivery of electrical stimulation signals. EMG signals are not necessarily evoked, and may be present without any delivery of electrical stimulation signals.

In some examples, EMG signals may be used to supplement and confirm determinations made based on the CMAP signals. For instance, the EMG of the airway, such as the genioglossal or geniohyoid muscle, may indicate that the muscles are tensing when breathing to indicate that therapy is appropriate. Also, because EMG signals can be measured without delivery of electrical stimulation signals, it may be possible to sense EMG signals and CMAP signals on same electrodes (e.g., electrodes sense EMG signals when not in response to delivery of stimulation, and CMAP signals in response to delivery of stimulation).

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 16 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

IMD 16 may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 60 may store the instructions (e.g., object code) of the software that processing circuitry 57 receives and executes, or another memory within IMD 16 (not shown) may store such instructions.

IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 56, processing circuitry 57, therapy delivery circuitry 58, switch circuitry 59, and telemetry circuitry 61 correspond to individual hardware units, such as ASICs, DSPs, FPGAs, or other hardware units.

Memory 60 stores therapy programs 63 (also called stimulation programs 63) that specify stimulation parameter values for the electrical stimulation provided by IMD 16. Memory 60 may also store instructions for execution by processing circuitry 57, in addition to stimulation programs 63. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 63. In some examples, processing circuitry 57 may select new stimulation parameters for a stimulation program 63 or new stimulation program from stimulation programs 63 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of therapy programs 63 to therapy delivery circuitry 58. For example, in operation, processing circuitry 57 may access memory 60 to load one of stimulation programs 63 to therapy delivery circuitry 58.

By way of example, processing circuitry 57 may access memory 60 to load one of stimulation programs 63 to control therapy delivery circuitry 58 for delivering the electrical stimulation to patient 14. A clinician or patient 14 may select a particular one of stimulation programs 63 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage or current pulse amplitude, a pulse rate, a pulse width, a duty cycle, and/or the combination of electrodes 30 that therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

In some examples, the stimulation parameters for the stimulation programs 63 may be selected to cause protrusor muscles 42 and/or 46 to an advanced state (e.g., to open-up airway 48). An example range of stimulation parameters for the electrical stimulation that are likely to be effective in treating OSA (e.g., upon application to the hypoglossal nerves to cause protrusor muscles 42, 46 to protrude or upon application to motor points such as motor points), are as follows:
  a. Frequency or pulse rate: between about 20 Hz and about 50 Hz, and possibly lower such as 2 Hz and 4 Hz. In some examples, the minimum target frequency is used which can achieve muscle tetany (e.g., constant contraction) and provide the required force to open the airway.
  b. Current Amplitude: between about 0.1 milliamps (mA) and about 20 mA, and more generally from 0.5 mA to 3 mA, and approximately 1.5 mA.
  c. Pulse Width: between about 100 microseconds (μs) and about 500 μs. In some examples, a pulse width of 150 μs might be used for reduced power consumption. In some particular examples, the pulse width is approximately 240 μs. In some cases, shorter pulse widths may be used in conjunction with higher current or voltage amplitudes.

Processing circuitry 57 may select stimulation programs 63 for alternating delivery of electrical stimulation between stimulating the left protrusor muscles 42 and/or 46 and the right protrusor muscles 42 and/or 46 on a time basis, such as in examples where lead 20 and lead 21 are implanted. In some examples, there may be some overlap in the delivery of electrical stimulation such that for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 57 may also select stimulation programs 63 that select between different combinations of electrodes 30 for stimulating, such as to stimulate different locations of the hypoglossal nerve(s), which may help with fatigue as well as provide more granular control of how much to protrude tongue 40.

In the example of FIG. 3, therapy delivery circuitry 58 drives electrodes 30 of lead 20 and electrodes 31 of lead 22. Specifically, therapy delivery circuitry 58 delivers electrical stimulation (e.g., regulated current or voltage pulses at pulse rates and pulse widths described above) to tissue of patient 14 via selected electrodes 30 carried by lead 20 or selected electrodes 31 carried by lead 22. A proximal end of lead 20 or 22 extends from the housing of IMD 16 and a distal end of lead 20 or 22 extends to a target therapy site, such as one or both hypoglossal nerves and/or motor points. Therapy delivery circuitry 58 may deliver electrical stimulation with electrodes on more than one lead and each of the leads may carry one or more electrodes, such as when patient 14 is implanted with leads 20 and 21 in tongue 40 for stimulating both hypoglossal nerves simultaneously or bilaterally (e.g., one after the other) or both motor points. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

In accordance with one or more examples described in this disclosure, processing circuitry 57 may be configured to determine therapeutic electrical stimulation parameters, such as updates to the electrical stimulation parameters stored in memory 60, using CMAP signals. As described above, there may be various causes for reduction in the efficacy of the electrical stimulation signals that are delivered for OSA treatment. In one or more examples, processing circuitry 57 may periodically (e.g., nightly or some other interval) determine appropriate therapeutic electrical stimulation parameters. In accordance with one or more examples described in this disclosure, processing circuitry 57 may utilize CMAP signals sensed by sensing circuitry 56 for determining the appropriate therapeutic electrical stimulation parameters.

In one or more examples, after processing circuitry 57 determines the therapeutic electrical stimulation parameters, therapy delivery circuitry 58 may deliver therapeutic electrical stimulation signals in accordance with the therapeutic electrical stimulation parameters for a certain duration of time. During this time, in some examples, IMD 16 may operate in an open-loop configuration where CMAP signals are not being sensed to save power consumption. After the duration of time, processing circuitry 57 may redetermine the therapeutic electrical stimulation parameters, and which point sensing circuitry 56 may sense the CMAP signals.

In one or more examples, therapy delivery circuitry 58 may be configured to output one or more electrical stimulation signals to tongue 40 of patient 14 via a first electrode (e.g., one of electrodes 30 or one of electrodes 31 in an alternative fashion) configured to be implantable within tongue 40. Sensing circuitry 56 may be configured to sense one or more CMAP signals via a second electrode (e.g., another one of electrodes 30 or electrodes 31) configured to be implantable within tongue 40. In some examples, the first and second electrodes may be the same electrodes. As described, the one or more CMAP signals are generated in response to the delivery of the one or more electrical stimulation signals.

In some examples, the electrical stimulation signal that therapy delivery circuitry 58 delivers for purposes of evoking the CMAP signals need not necessarily be therapeutic. That is, the electrical stimulation signal that is delivered to evoke the CMAP signal may not cause tongue 40 to advance and open the airflow. However, by sensing the CMAP signals, and determining when there is a change in the CMAP signals, processing circuitry 57 may determine the therapeutic electrical stimulation parameters. The therapeutic electrical stimulation parameters refer to electrical stimulation parameters that when delivered cause tongue 40 to advance and provide OSA treatment.

As an example, processing circuitry 57 may be configured to cause therapy delivery circuitry 58 to output the one or more electrical stimulation signals to tongue 40. As an example, processing circuitry 57 may sweep the energy (e.g., amplitude, frequency, and/or pulse width) of the one or more electrical stimulation signals that are delivered to tongue 40 starting with a low amplitude and increasing the amplitude over time.

Processing circuitry 57 may receive information indicative of the one or more CMAP signals from sensing circuitry 56. As one example, and as described in more detail with respect to FIGS. 7A and 7B, processing circuitry 57 may cause therapy delivery circuitry 58 to deliver a plurality of electrical stimulation signals at a first amplitude, and processing circuitry 57 may receive information indicative of each of the CMAP signals generated in response to the electrical stimulation signals delivered at the first amplitude. Processing circuitry 57 may cause therapy delivery circuitry 58 to deliver a plurality of electrical stimulation signals at a second amplitude, and processing circuitry may receive information indicative of each of the CMAP signals generated in response to the electrical stimulation signals delivered at the second amplitude, and so forth.

In some examples, sensing circuitry 56 may be configured to low-pass filter the sensed signal since signal content that is less than 1 kHz may be the CMAP signal content of interest. That is, the band of response for the CMAP signal may be less than 1 kHz, but the example techniques should not be considered limited. Sensing circuitry 56 may be configured to perform some artifact cancellation, such as sum exponentials, or other known artifact cancellation techniques to reduce the noise in the CMAP signal.

Moreover, to sense the CMAP signal, sensing circuitry 56 may be configured to sense the CMAP signal within a certain window of time. For instance, after therapy delivery circuitry 58 delivers a stimulation signal, switch circuitry 59 may configure electrodes 30 or 31 through a discharge phase to remove residual charge that can impact the capabilities of sensing circuitry 56 to sense the CMAP signal. As one example, switch circuitry 59 may couple electrodes 30 or 31 to ground to allow the charge on electrodes 30 or 31 to dissipate, in accordance with passive discharge. As another example, switch circuitry 59 may couple electrodes 30 or 31 to allow therapy delivery circuitry 58 to deliver an electrical signal having the opposite phase as the electrical stimulation signal in accordance with active discharge. In some examples, switch circuitry 59 may couple electrodes 30 or 31 for truncated passive discharge, in which, electrodes 30 or 31 are coupled to ground to allow electrodes 30 or 31 to discharge, but not fully discharge. After electrodes 30 or 31 discharge to a certain level that does not impact sensing, sensing circuitry 56 may sense the CMAP signal, after which, electrodes 30 or 31 may be fully discharged.

In accordance with one or more examples described in this disclosure, processing circuitry 57 may determine, based on the one or more CMAP signals, one or more therapeutic stimulation parameters for the OSA treatment. For example, as the strength of the stimulation (e.g., amplitude, frequency, and/or pulse width) is increased, the amplitude of the CMAP signal also increases. However, when tongue 40 moves, and particularly, when tongue 40 moves in the therapeutic position, the CMAP signal shape and amplitude may change. The changes in the CMAP shape and amplitude may result in increases in variance of the CMAP signals recorded over a fixed time. The variance may be a measure of how much tongue 40 moves within a unit of time, or the first derivative of the tongue movement.

As described above, the one or more CMAP signals may include an artifact portion and a non-artifact portion. Processing circuitry 57 may determine that there is a change in the CMAP signals based on changes in both the artifact and non-artifact portions, changes in just the non-artifact portions, or changes in the just the artifact portions (e.g., if there is a non-linear change in the artifact portions).

In one or more examples, processing circuitry 57 may cause the strength (e.g., amplitude) of the electrical stimulation signal to slowly increase, and processing circuitry 57 may determine amplitude of CMAP signals, shape of CMAP signals, and/or increase in variance of CMAP signals to constant stimulation. Processing circuitry 57 may utilize the amplitude, shape, and variance information to determine the therapeutic electrical stimulation parameters.

In this disclosure, there may be a change in the CMAP shape and/or amplitude as there is a change in the strength of the electrical stimulation signal. The variance of the CMAP signal may change, however, even with the same constant stimulation. For instance, therapy delivery circuitry 58 may deliver electrical stimulation signals at one amplitude for a period of time. During this period of time, the variance of the CMAP signals measured through the period of time may change. In one or more examples, change in CMAP signals includes examples where there is change in one or more of an amplitude between the two or more of the CMAP signals, a shape between the two or more of the CMAP signals, and whether there is a change in a variance between the two or more of the CMAP signals.

For example, to cause therapy delivery circuitry 58 to output the one or more electrical stimulation signals, processing circuitry 57 is configured to cause therapy delivery circuitry 58 to output a plurality of electrical stimulation signals having different energy (e.g., strength). To receive information indicative of the one or more CMAP signals, processing circuitry 57 may be configured to receive information indicative of each of a plurality of CMAP signals each generated in response to a respective one of the plurality of electrical stimulation signals. Processing circuitry 57 may be configured to compare two or more of the plurality of CMAP signals to each other (e.g., to one another).

To determine the one or more therapeutic stimulation parameters based on the one or more CMAP signals for OSA treatment, processing circuitry 57 may be configured to determine the one or more therapeutic stimulation parameters based on the comparison. As an example, to determine the one or more therapeutic stimulation parameters based on the comparison, processing circuitry 57 may be configured to determine for which one of the two or more of the plurality of CMAP signals there is a change relative to another one of the two or more of the plurality of CMAP signals, determine an electrical stimulation signal of the plurality of electrical stimulation parameters that generated the determined one of the plurality of CMAP signals, determine one or more stimulation parameters for the determined electrical stimulation signal, and determine the one or more therapeutic stimulation parameters based on the determined one or more stimulation parameters. For example, if the amplitude of the electrical stimulation signal that caused the change in the CMAP signals is 2.3 mA, then processing circuitry 57 may determine that the amplitude of the therapeutic electrical stimulation signal should be 2.3 mA.

Processing circuitry 57 may cause therapy delivery circuitry 58 to deliver therapeutic electrical stimulation signals according to at least the determined one or more therapeutic stimulation parameters. In this way, patient 14 may receive OSA treatment with stimulation parameters selected that may ensure the therapy is effective, while minimizing power consumption and reducing clinic visits.

The above example techniques are described with examples for determining the therapeutic electrical stimulation parameters based on CMAP signals. However, the example techniques are not so limited. In some examples, processing circuitry 57 may utilize the CMAP signals to determine the tone of tongue 40 while the patient is sleeping. For instance, processing circuitry 57 may utilize the CMAP signals to determine if tongue 40 is fatiguing so that changes to therapy can be made to address the fatigue.

As an example, the amount of time used to determine the therapeutic electrical stimulation parameters may be in the order of a few seconds (e.g., less than 10 seconds, less than a minute). However, after therapy is being delivered, and tongue 40 is in the advance state, there may be changes in the CMAP signals.

Some decay in the CMAP signals during therapy delivery may be expected, such as after 250-300 seconds. This may be due to the different fibers and how long different fibers take to fatigue. However, after a longer while, such as 1000 seconds and more, rather than having a decaying CMAP signal, the amplitude of the CMAP signal may decrease, and the variance of the CMAP signal may also increase. This decrease in amplitude of the CMAP signal may correspond to loss of therapy, which might be due to restructuring of tissue or movement of leads 20 and 22. The increase in amplitude of the CMAP signal may be indicative of fatigue of tongue 40. In some examples, the fatigue of the tongue results in tongue 40 wobbling, causing a change in CMAP signal shape and increase of variance.

In addition, if tongue 40 collapses, then the stimulation may not produce motion of tongue 40. When stimulation switches from one side to another side of tongue 40, there might be an expectation of a corresponding small motion of tongue 40, which would be indicative by slight variance in the CMAP signal. However, in the condition that the stimulation is ineffective, this variance may not occur. Thus, abnormally low variance of the CMAP may be indicative of tongue collapse. In other words, in some examples, normal function may be indicated by variance of the CMAP signal being contained in a specified range (e.g. between 10% and 20% of the CMAP signal).

The processing circuitry may utilize a lack of change in the CMAP to infer that there is no motion of tongue 40 (e.g., there is possible of tongue collapse). For instance, after determining the therapeutic stimulation parameters, and sweeping from low energy to the energy level consistent with the determined therapeutic stimulation parameters, if there is no change in the CMAP signal, there is a possibility of tongue collapse (e.g., due to fatigue or other causes). In such examples, the processing circuitry may increase therapy energy (e.g., higher amplitude, frequency, and/or pulse width than was previously determined up to full-strength therapy) or rescue therapy.

In some examples, the one or more CMAP signals that were used to determine the therapeutic electrical stimulation parameters may be considered as a first set of one or more CMAP signals. In one or more examples, subsequent to the delivery of the therapeutic electrical stimulation signals, processing circuitry 57 may be configured to receive information indicative of a second set of CMAP signals generated in response to the delivery of the therapeutic electrical stimulation signals. Processing circuitry 57 may compare two or more CMAP signals of the second set of CMAP signals with each other (e.g., to one another), and determine that the tongue is experiencing fatigue based on the comparison. Processing circuitry 57 may control therapy delivery circuitry 58 based on the determination that tongue 40 is experiencing fatigue.

To determine that tongue 40 is experiencing fatigue, processing circuitry 57 may compare the second set of CMAP signals in a similar way as the first set of CMAP signals described above. For instance, to compare the two or more CMAP signals of the second set of CMAP signals with each other (e.g., to one another), processing circuitry 57 may be configured to determine whether there is a change in one or more of an amplitude between the two or more of the second set of CMAP signals, a shape between the two or more of the second set of CMAP signals, and whether there is a change in a variance between the two or more of the second set of CMAP signals. In some examples, whether the variance of the CMAP signals is within a particular range may be indicative of movement of tongue 40, such as if tongue 40 is experiencing fatigue.

In some examples, processing circuitry 57 may automatically increase the amplitude of the therapeutic electrical stimulation signal when fatigue is detected. For example, processing circuitry 57 may be configured to update one or more of the one or more stimulation parameters to generate updated one or more stimulation parameters based on the comparison that indicated that tongue 40 is fatigued. Processing circuitry 57 may cause therapy delivery circuitry 58 to deliver updated therapeutic electrical stimulation signals based on the updated one or more stimulation parameters. In some examples, processing circuitry 57 may sweep through the amplitude, frequency, and/or pulse width and determine the CMAP signals, as described above, to determine updated one or more stimulation parameters.

In some examples, processing circuitry 57 may adjust the timing of how long each side of tongue 40 is to be stimulated when tongue 40 is fatiguing. For example, tongue 40 may stimulate the left side of tongue 40 for longer, allowing the right side of tongue 40 to rest, or vice-versa. In some examples, processing circuitry 57 may stimulate a single side, rather than bilateral stimulation (e.g. stimulating both sides), based on disease state.

However, in some examples, rather than increasing or updating the stimulation parameters, patient 14 may benefit from a temporary cessation of therapy to allow tongue 40 to rest. For instance, to control therapy delivery circuitry 58, processing circuitry 57 may be configured to cause therapy delivery circuitry 58 to cease delivery of the therapeutic electrical stimulation signals. After some time, processing circuitry 57 may redetermine the therapeutic electrical stimulation parameters using the example techniques described above such as by sweeping the strength of the electrical stimulation signal, measuring the CMAP signals, and determine the electrical stimulation signal at which point the CMAP signals changed. The processing circuitry may determine the therapeutic electrical stimulation signal parameters based on the parameters of the electrical stimulation signal that caused the CMAP signals to change.

Figure 4:
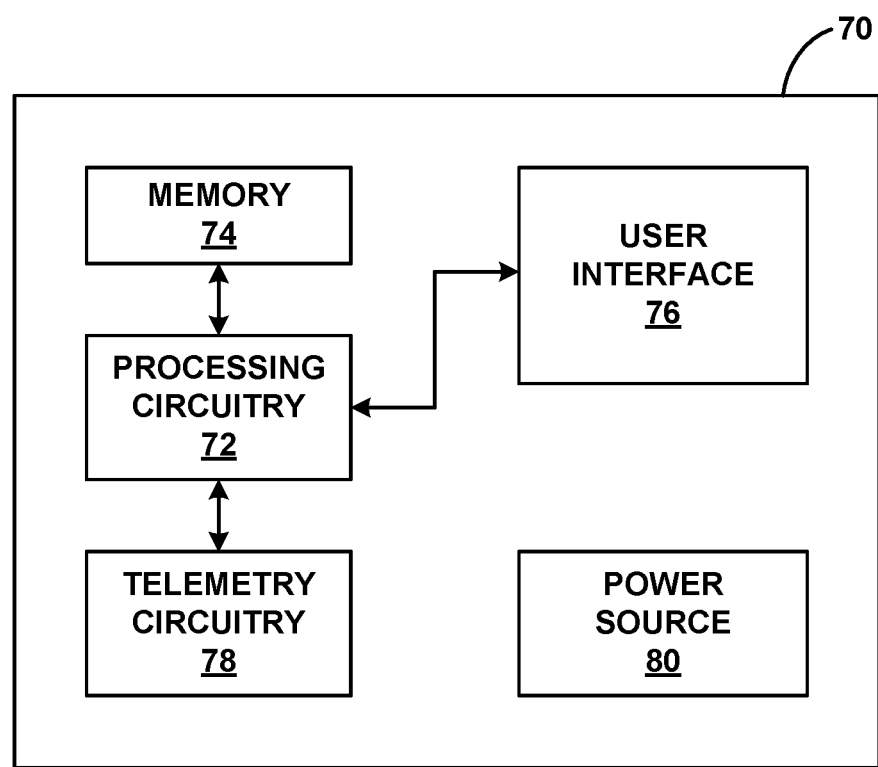
FIG. 4 is a block diagram illustrating an example configuration of an external programmer.

FIG. 4 is a block diagram illustrating an example configuration of an external programmer 70. While programmer 70 may generally be described as a hand-held computing device, the programmer may be a notebook computer, a cell phone, or a workstation, for example. As illustrated in FIG. 4, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 78 may include an antenna, which may take on a variety of forms, such as an internal or external antenna.

Examples of local wireless communication techniques that may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

In one or more examples, processing circuitry 72 may be configured to perform at least some of the functions of processing circuitry 57, possibly in conjunction with processing circuitry 57. For instance, IMD 16 may transmit information such as information indicative of CMAP signals to programmer 70. Processing circuitry 72 may evaluate the CMAP signals (e.g., compare CMAP signals to determine if there is a change), and determine therapeutic electrical stimulation parameters similar to the description for processing circuitry 57.

Accordingly, in one or more example, the processing circuitry that may be configured to perform the example techniques described in this disclosure includes processing circuitry 57, processing circuitry 72, or a combination of processing circuitry 57 and processing circuitry 72. For instance, the example techniques may be performed in a medical system that includes IMD 16, where IMD 16 includes therapy delivery circuitry 58, sensing circuitry 56, and at least a portion of the processing circuitry (e.g., processing circuitry 57). In some examples, the example techniques may be performed in a medical system that includes IMD 16 and external programmer 70. IMD 16 includes therapy delivery circuitry 58 and sensing circuitry 56, and external programmer 70 includes at least a portion of the processing circuitry (e.g., processing circuitry 72).

Figure 5:
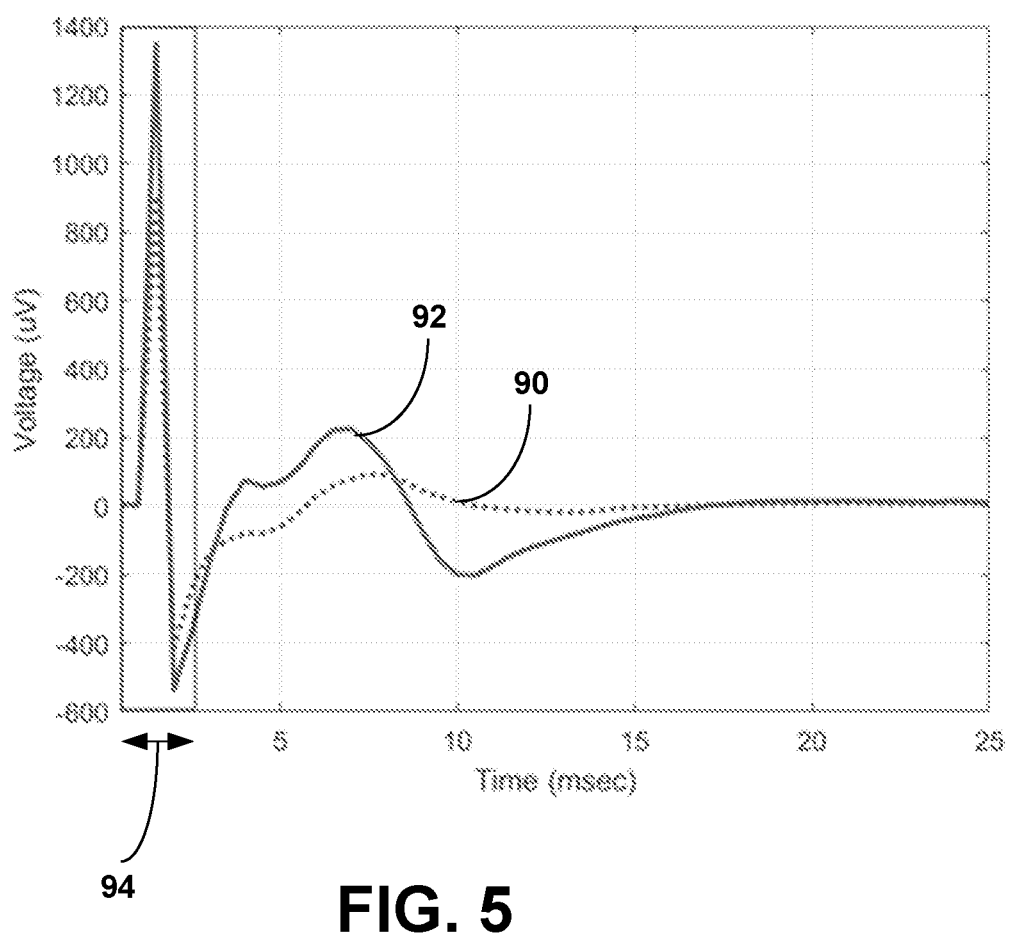
FIG. 5 is a graph illustrating an example of a CMAP signal prior to the tongue being in the advanced state and after the tongue being in the advance state.

FIG. 5 is a graph illustrating an example of a CMAP signal prior to the tongue being in the advanced state and after the tongue being in the advance state. In the example of FIG. 5, CMAP signal 90 represents an example of the CMAP signal prior to tongue 40 being in an advanced state. CMAP signal 92 represents an example of the CMAP signal after tongue 40 is in the advanced state. As can be seen, there is a change in the morphology of the CMAP signal after the tongue moves to the advanced state. For instance, CMAP signal 92 and CMAP signal 90 are different, such as in amplitude, frequency, etc. In one or more example, processing circuitry may be configured to determine the change in the CMAP signal to determine that tongue 40 is in the advanced state. FIG. 5 also illustrates time period 94 during which there may be artifacts in the CMAP signal. Artifacts may be signal components not reflective of the compound muscle action potentials from muscle, such as direct detection or representation of a bi-phasic (e.g., positive and negative polarity) stimulation pulse delivered from IMD 16. However, other causes of the artifacts are possible, and the example techniques should not be considered limited. Such artifacts may be filtered or the processing circuitry may evaluate CMAP signal 90 and 92 after a certain amount of time to allow the artifacts to be suppressed or otherwise removed from the respective signals 90 and 92.

However, in some examples, the processing circuitry may utilize changes in the artifact portion of the CMAP signals to determine if there is a change in the CMAP signal. For instance, as illustrated in FIG. 5, the artifact portion, represented by time period 94, is approximately within the first 3 milliseconds, and tends to have high frequency content and relatively high amplitude. The artifact portion may increase linearly with increase in stimulation, without movement of tongue 40. However, when there is movement of tongue 40, the artifact portion may increase non-linearly. Accordingly, by evaluating change in the artifact portion, the processing circuitry may determine if there is movement of tongue 40.

Figure 6:
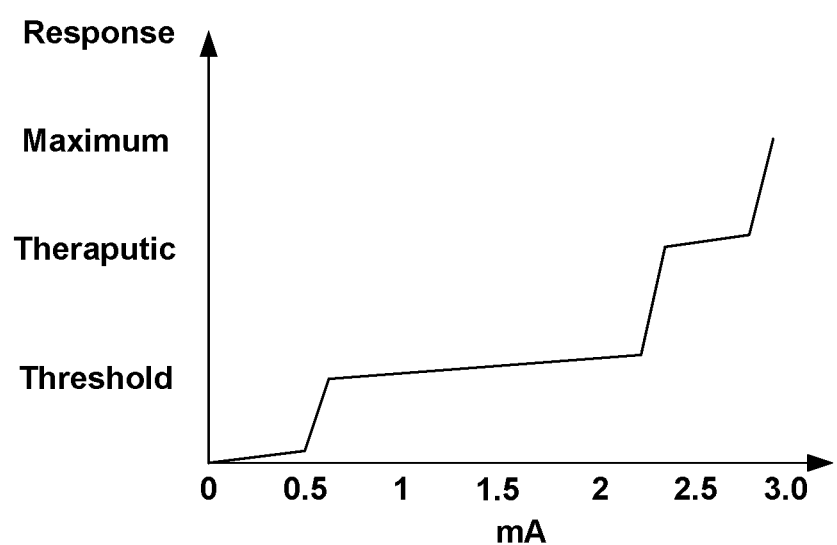
FIG. 6 is a graph illustrating an example of amplitude of electrical stimulation signal and response of tongue to the electrical stimulation signal.

FIG. 6 is a graph illustrating an example of amplitude of electrical stimulation signal and response of tongue to the electrical stimulation signal. For instance, the y-axis in FIG. 6 illustrates that response of tongue 40, and the x-axis in FIG. 6 illustrates the amplitude of the electrical stimulation signal. As the amplitude is increased, tongue 40 does not move much until about 0.6 mA, at which point the amplitude is at such a level that movement of tongue 40 is noticeable. However, tongue 40 has not moved sufficient to provide therapeutic benefit.

At approximate 2.3 mA, tongue 40 advances sufficiently to open up airflow and provide therapeutic results and treatment for OSA. At approximately 3 mA, tongue 40 is advanced maximally. In some cases, it may be possible to deliver therapy at 3 mA, but at such a level there may be relatively high power drain. With the example techniques described in this disclosure, processing circuitry 57 or 72 may be configured to determine that an amplitude of approximately 2.3 mA is sufficient to provide effective therapy, and may be configured to determine the amplitude without requiring a clinic visit. For instance, processing circuitry 57 or 72 may utilize CMAP signals to determine the effective amplitude.

Figure 7A:
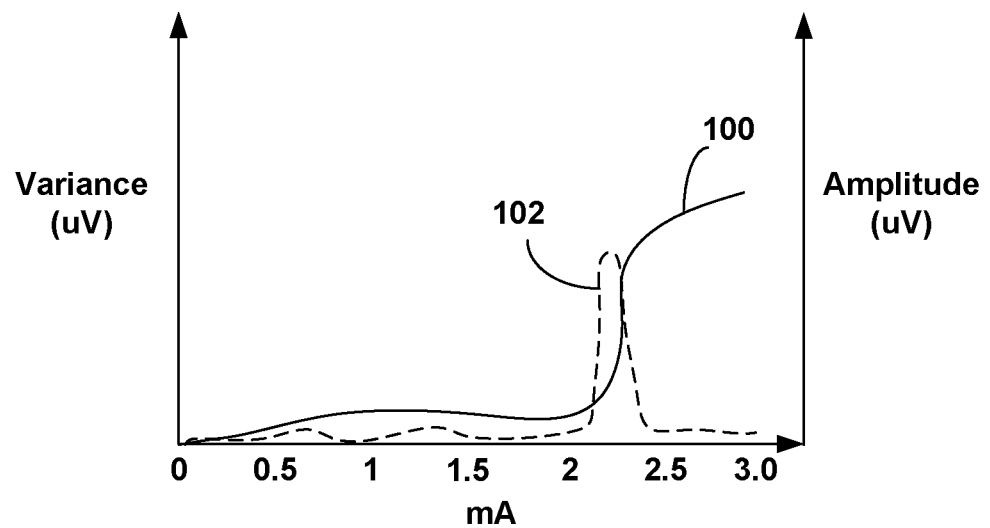
FIGS. 7A and 7B are graphs illustrating examples of amplitude and variance of CMAP signals as a function of amplitude of the electrical stimulation signal.
Figure 7B:
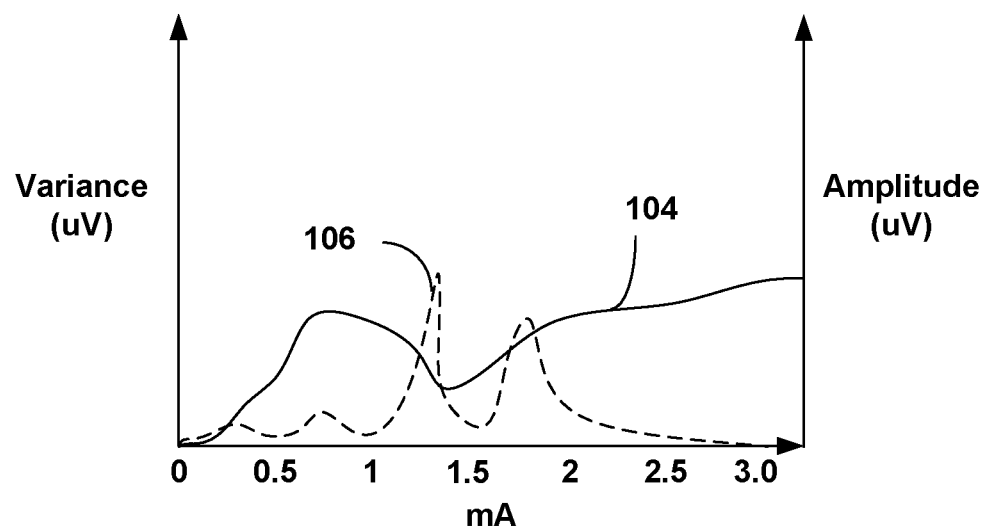

FIGS. 7A and 7B are graphs illustrating examples of amplitude and variance of CMAP signals as a function of amplitude of the electrical stimulation signal. FIGS. 7A and 7B are generated by delivering stimulation at a set amplitude (e.g., 0.5 mA, 1 mA, 1.5 mA, and so forth) for a set amount of time (e.g., one second). During that one section, therapy delivery circuitry 58 may deliver forty electrical stimulation signals, and sensing circuitry 56 may sense forty CMAP signals. The non-dashed lines 100 in FIG. 7A and 104 in FIG. 7B represent the average of the CMAP amplitude across the forty CMAP signals at the particular stimulation amplitude. The dashed lines 102 in FIG. 7A and 106 in FIG. 7B represent the variance of the forty CMAP signals at the particular stimulation amplitude. As described, the variance may be a measure of how much the tongue moves within a unit of time, or the first derivative of the tongue movement. For instance, the variance at a particular amplitude may be a measure of amount by which the CMAP signal amplitude changed within the one second interval during which the forty CMAP signals were measured. The use of forty electrical stimulation signals, and forty CMAP signals is provided simply to assist with understanding, and should not be considered limiting.

As can be seen in FIG. 7A, as the amplitude of the electrical stimulation signal is increased, at approximately 2.3 mA, the amplitude 100 of the CMAP signal increases dramatically. Similarly, in FIG. 7A, at approximately 2.3 mA, the variance 102 suddenly changes. The amplitude of 2.3 mA, where the amplitude 100 and the variance 102 of the CMAP signal in FIG. 7A increases corresponds to the 2.3 mA of FIG. 6 where tongue 40 advances for a therapeutic response. More than 2.3 mA of amplitude, and there is not much more tongue movement within a unit of time, and therefore, the variance drops down again. Accordingly, by determining if there is a change in the CMAP amplitude or variance, it may be possible to determine the amplitude of electrical stimulation signal that provides therapeutic benefit.

In some cases, the movement of tongue 40 may be more complex than in the example of FIG. 7A. For instance, in the example of FIG. 7B, tongue 40 had two different motions. In one motion, the airway did not fully open, but there was a sudden change in amplitude and variance of the CMAP signal. The example of FIG. 7B may be a less typical case, and may be a factor of which electrodes are used for sensing. However, even in examples such as FIG. 7B, it may be possible to use the CMAP signal to determine therapeutic electrical stimulation parameters.

For instance, during a clinician visit, a clinician may measure CMAP signals over a sweep of amplitudes, frequency, and/or pulse width for the electrical stimulation signal. The clinician may determine when tongue 40 has move sufficiently to determine therapeutic electrical stimulation parameters. Processing circuitry 57 or 72 may store the CMAP signal pattern over the sweep. During normal operation, processing circuitry 57 or 72 may match the CMAP signal pattern that is measured during normal operation to the CMAP signal pattern generated during the clinic visit. Based on whether the CMAP signal pattern is a match or not, processing circuitry 57 or 72 may determine the therapeutic electrical stimulation parameters.

Figure 8:
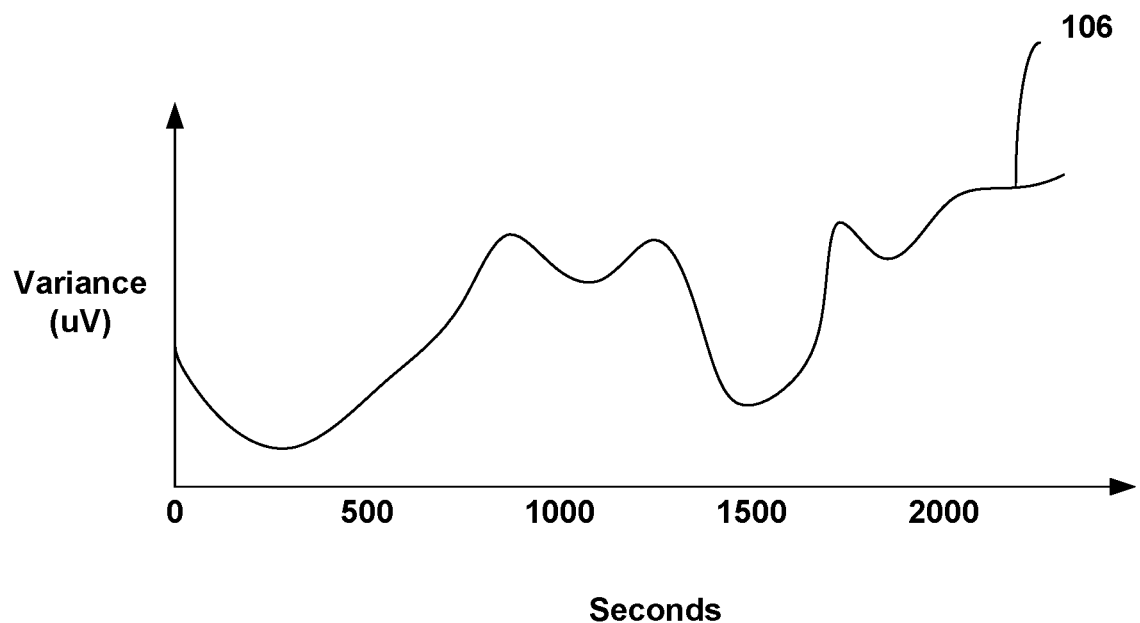
FIG. 8 is a graph illustrating a variance in CMAP signals as a function of time during delivery of stimulation.
Figure 9:
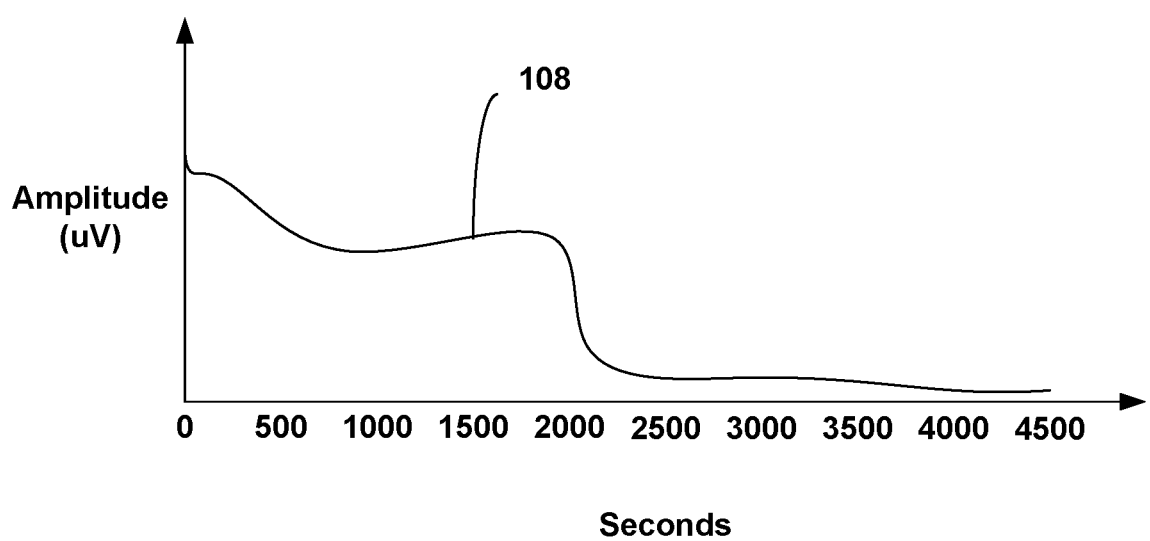
FIG. 9 is a graph illustrating an amplitude of CMAP signals as a function of time during delivery of stimulation.

FIG. 8 is a graph illustrating a variance in CMAP signals as a function of time during delivery of stimulation. FIG. 9 is a graph illustrating an amplitude of CMAP signals as a function of time during delivery of stimulation. For instance, FIGS. 8 and 9 illustrate the variance in the CMAP signals and the amplitude of CMAP signals, respectively, while patient 14 is asleep and tongue 40 may be getting fatigued. For instance, as shown in FIG. 8, over an extended period of time, as tongue 40 beings to fatigue, the variance 106 starts to increase. Similarly, in FIG. 9, over an extended period of time, there can be a sudden change in the CMAP signal, such as around after 2000 seconds, rather than a slow decay in the CMAP amplitude, which indicates that tongue 40 is fatiguing.

Figure 10:
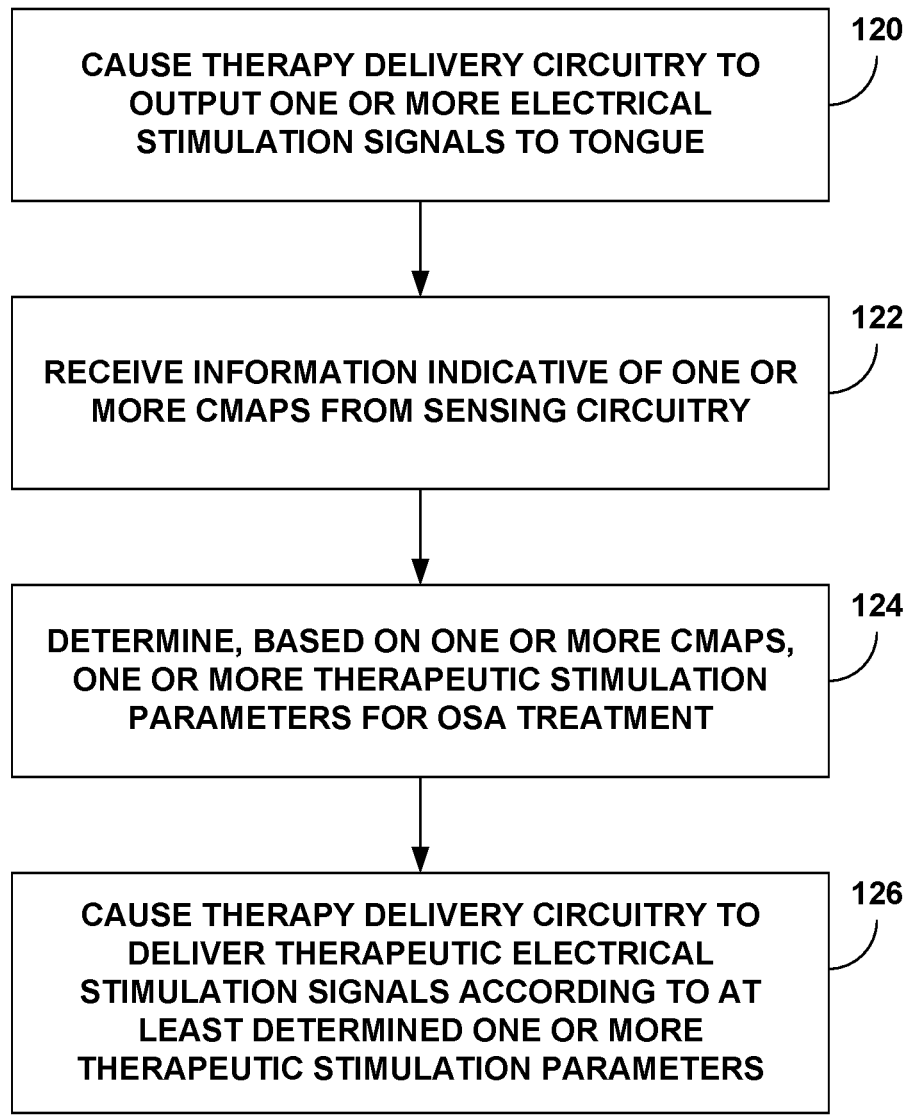
FIG. 10 is a flowchart illustrating an example of method of operation for OSA treatment.

FIG. 10 is a flowchart illustrating an example of method of operation for OSA treatment. The example of FIG. 10 is described with respect to processing circuitry, examples of which include processing circuitry 57 and 72.

The processing circuitry may be configured to cause therapy delivery circuitry 58 to output one or more electrical stimulation signals to tongue 40 of patient 14 via a first electrode configured to be implantable within tongue 40 (120). For example, to cause therapy delivery circuitry 58 to output the one or more electrical stimulation signals, the processing circuitry may be configured to cause therapy delivery circuitry 58 to output a plurality of electrical stimulation signals having different energy (e.g., different strengths or different amplitudes).

The processing circuitry may be configured to receive, from sensing circuitry 56, one or more compound muscle action potential (CMAP) signals via a second electrode configured to be implantable within tongue 40 (122). As described, the one or more CMAP signals may be generated in response to the delivery of the one or more electrical stimulation signals. To receive information indicative of the one or more CMAP signals, the processing circuitry may be configured to receive information indicative of each of a plurality of CMAP signals each generated in response to a respective one of the plurality of electrical stimulation signals.

The processing circuitry may be configured to determine, based on the one or more CMAP signals, one or more therapeutic stimulation parameters for the OSA treatment (124). For example, the processing circuitry may be configured to compare two or more of the plurality of CMAP signals to each other (e.g., to one another). To determine the one or more therapeutic stimulation parameters based on the one or more CMAP signals for OSA treatment, the processing circuitry may be configured to determine the one or more therapeutic stimulation parameters based on the comparison.

As an example, to determine the one or more therapeutic stimulation parameters based on the comparison, the processing circuitry may be configured to determine for which one of the two or more of the plurality of CMAP signals there is a change relative to another one of the two or more of the plurality of CMAP signals, or if there is not a change when a change is expected. The processing circuitry may be configured to determine an electrical stimulation signal of the plurality of electrical stimulation parameters that generated the determined one of the plurality of CMAP signals, determine one or more stimulation parameters for the determined electrical stimulation signal, and determine the one or more therapeutic stimulation parameters based on the determined one or more stimulation parameters. In some examples, the change includes a change in one or more of an amplitude between the two or more of the plurality of CMAP signals, a shape between the two or more of the plurality of CMAP signals, and whether there is a change in a variance between the two or more of the plurality of CMAP signals.

The processing circuitry may cause therapy delivery circuitry 58 to deliver therapeutic electrical stimulation signals according to at least the determined one or more therapeutic stimulation parameters (126). In this manner, the processing circuitry may deliver therapeutic electrical stimulation signals based on CMAP signals.

Figure 11:
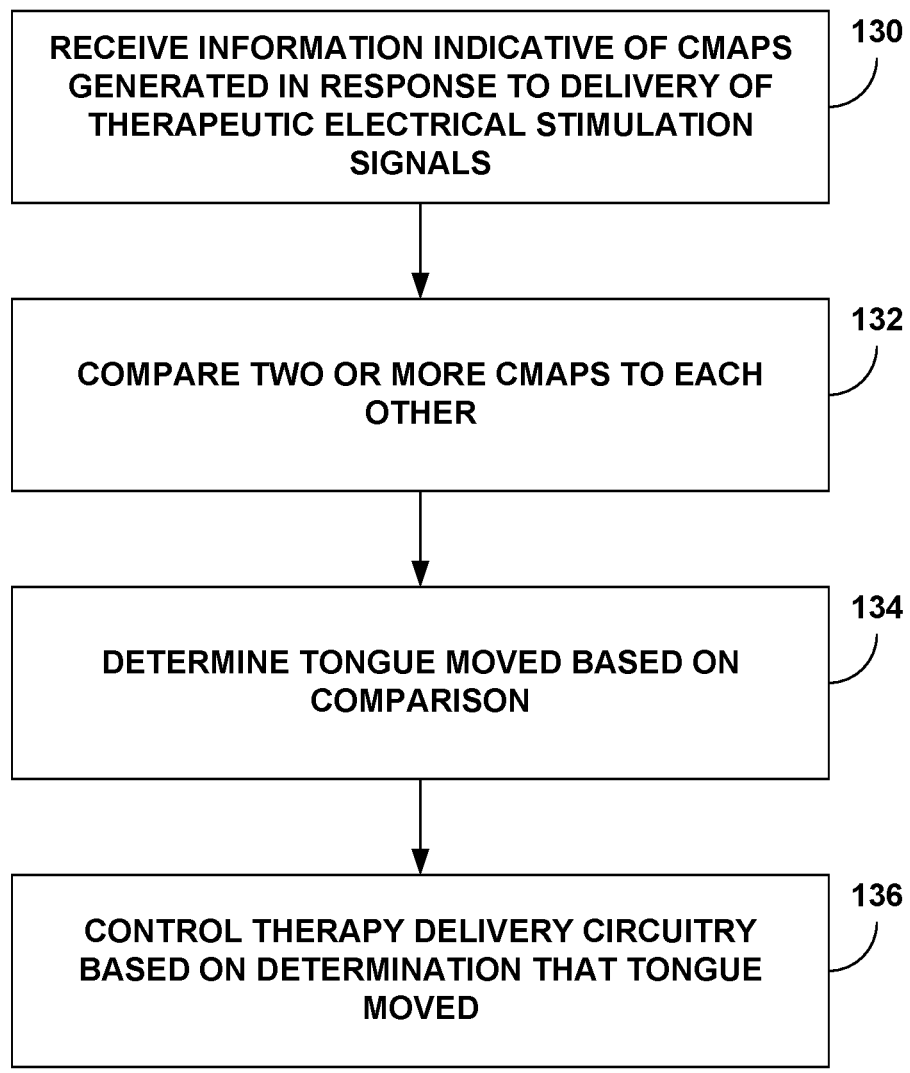
FIG. 11 is another flowchart illustrating an example of method of operation for OSA treatment.

FIG. 11 is another flowchart illustrating an example of method of operation for OSA treatment. The example of FIG. 11 is described with respect to processing circuitry, examples of which include processing circuitry 57 and 72. The one or more CMAP signals of FIG. 10 may be considered as a first set of one or more CMAP signals. The processing circuitry may be configured to perform the example techniques of FIG. 11 subsequent to the delivery of the therapeutic electrical stimulation signals.

The processing circuitry may receive information indicative of a second set of CMAP signals generated in response to the delivery of the therapeutic electrical stimulation signals (130). For instance, the processing circuitry may receive the second set of CMAP signals similar to the manner in which the processing circuitry received the first set of CMAP signals.

The processing circuitry may compare two or more CMAP signals of the second set of CMAP signals to each other (e.g., to one another) (132). For example, the processing circuitry may compare the two or more CMAP signals of the second set of CMAP signals similar to the first set of CMAP signals. As an example, to compare the two or more CMAP signals of the second set of CMAP signals with each other (e.g., to one another), the processing circuitry may be configured to determine whether there is a change in one or more of an amplitude between the two or more of the second set of CMAP signals, a shape between the two or more of the second set of CMAP signals, and whether there is a change in a variance between the two or more of the second set of CMAP signals.

The processing circuitry may determine that tongue 40 moved based on the comparison (134). For example, the processing circuitry may determine that tongue 40 is experiencing fatigue based on the comparison. For example, if the processing circuitry determines that there is an increase in the variance, or a sudden change in the amplitude of the CMAP signal, the processing circuitry may determine that tongue 40 is experiencing fatigue. Fatigue is provided as one example, and in the example techniques, tongue 40 may move for other reasons as well, such as a shift in tongue position (e.g., due to movement by the patient).

The processing circuitry may control therapy delivery circuitry 58 based on the determination that tongue 40 moved (136). For example, the processing circuitry may control therapy delivery circuitry 58 based on the determination that tongue 40 is experiencing fatigue. As one example, to control the therapy delivery circuitry, the processing circuitry may be configured to update one or more of the one or more stimulation parameters to generate updated one or more stimulation parameters based on the comparison, and cause therapy delivery circuitry 58 to deliver updated therapeutic electrical stimulation signals based on the updated one or more stimulation parameters. As another example, to control the therapy delivery circuitry, the processing circuitry may be configured to cause therapy delivery circuitry 58 to cease delivery of the therapeutic electrical stimulation signals.

The following describes some example techniques that may be used separately or together.

Example 1. A medical system for obstructive sleep apnea (OSA) treatment, the system comprising: therapy delivery circuitry configured to output one or more electrical stimulation signals to a tongue of a patient via a first electrode configured to be implantable within the tongue; sensing circuitry configured to sense one or more compound muscle action potential (CMAP) signals via a second electrode configured to be implantable within the tongue, wherein the one or more CMAP signals are generated in response to the delivery of the one or more electrical stimulation signals; and processing circuitry configured to: cause the therapy delivery circuitry to output the one or more electrical stimulation signals to the tongue; receive information indicative of the one or more CMAP signals from the sensing circuitry; determine, based on the one or more CMAP signals, one or more therapeutic stimulation parameters for the OSA treatment; and cause the therapy delivery circuitry to deliver therapeutic electrical stimulation signals according to at least the determined one or more therapeutic stimulation parameters.

Example 2. The medical system of example 1, further comprising an implantable medical device (IMD), wherein the IMD includes the therapy delivery circuitry, the sensing circuitry, and at least a portion of the processing circuitry.

Example 3. The medical system of example 1, further comprising an implantable medical device (IMD) and an external programmer, wherein the IMD includes the therapy delivery circuitry and the sensing circuitry, and wherein the external programmer includes at least a portion of the processing circuitry.

Example 4. The medical system of any of examples 1-3, wherein to cause the therapy delivery circuitry to output the one or more electrical stimulation signals, the processing circuitry is configured to cause the therapy delivery circuitry to output a plurality of electrical stimulation signals having different energy, wherein to receive information indicative of the one or more CMAP signals, the processing circuitry is configured to receive information indicative of each of a plurality of CMAP signals each generated in response to a respective one of the plurality of electrical stimulation signals, wherein the processing circuitry is configured to compare two or more of the plurality of CMAP signals to each other, and wherein to determine the one or more therapeutic stimulation parameters based on the one or more CMAP signals for OSA treatment, the processing circuitry is configured to determine, based on the comparison, the one or more therapeutic stimulation parameters.

Example 5. The system of example 4, wherein to determine, based on the comparison, the one or more therapeutic stimulation parameters, the processing circuitry is configured to: determine for which one of the two or more of the plurality of CMAP signals there is a change relative to another one of the two or more of the plurality of CMAP signals; determine an electrical stimulation signal of the plurality of electrical stimulation parameters that generated the determined one of the plurality of CMAP signals; determine one or more stimulation parameters for the determined electrical stimulation signal; and determine the one or more therapeutic stimulation parameters based on the determined one or more stimulation parameters.

Example 6. The system of example 5, wherein the change includes a change in one or more of an amplitude between the two or more of the plurality of CMAP signals, a shape between the two or more of the plurality of CMAP signals, and whether there is a change in a variance between the two or more of the plurality of CMAP signals.

Example 7. The system of any of examples 1-6, wherein the one or more CMAP signals comprise a first set of one or more CMAP signals, and wherein, subsequent to the delivery of the therapeutic electrical stimulation signals, the processing circuitry is configured to: receive information indicative of a second set of CMAP signals generated in response to the delivery of the therapeutic electrical stimulation signals; compare two or more CMAP signals of the second set of CMAP signals to each other; determine that the tongue is experiencing fatigue based on the comparison; and control the therapy delivery circuitry based on the determination that the tongue is experiencing fatigue.

Example 8. The system of example 7, wherein to control the therapy delivery circuitry, the processing circuitry is configured to: update one or more of the one or more stimulation parameters to generate updated one or more stimulation parameters based on the comparison; and cause the therapy delivery circuitry to deliver updated therapeutic electrical stimulation signals based on the updated one or more stimulation parameters.

Example 9. The system of example 7, wherein to control the therapy delivery circuitry, the processing circuitry is configured to: cause the therapy delivery circuitry to cease delivery of the therapeutic electrical stimulation signals.

Example 10. The system of any of examples 7-9, wherein to compare the two or more CMAP signals of the second set of CMAP signals to each other, the processing circuitry is configured to determine whether there is a change in one or more of an amplitude between the two or more of the second set of CMAP signals, a shape between the two or more of the second set of CMAP signals, and whether there is a change in a variance between the two or more of the second set of CMAP signals.

Example 11. The system of any of examples 1-10, further comprising an accelerometer configured to generate information indicative of patient posture, wherein the processing circuitry is configured to receive the information indicative of patient posture, and determine whether there is a change in posture based on the received information, and wherein the processing circuitry is configured to, in response to the determination that there is the change in posture: cause the therapy delivery circuitry to output the one or more electrical stimulation signals to the tongue; receive the information indicative of the one or more CMAP signals from the sensing circuitry; and determine the one or more therapeutic stimulation parameters based on the one or more CMAP signals for the OSA treatment.

Example 12. The system of any of examples 1-11, wherein the one or more CMAP signals includes an artifact portion and a non-artifact portion, wherein to determine the one or more therapeutic stimulation parameters, the processing circuitry is configured to determine the one or more therapeutic stimulation parameters based on: both the artifact portion and the non-artifact portion of the one or more CMAP signals; the non-artifact portion of the one or more CMAP signals, and not the artifact portion; or the artifact portion of the one or more CMAP signals, and not the non-artifact portion.

Example 13. The system of any of examples 1-12, wherein to receive information indicative of the CMAP signals, the processing circuitry is configured to receive a first CMAP signal evoked on a first side of a tongue with a first electrode, a second CMAP signal evoked on one of a second side of the tongue or on the first side of the tongue with a second electrode, and a combined CMAP signal simultaneously evoked on both the first side and the second side or evoked on the first side with stimulation from all electrodes on the first side, wherein to determine one or more therapeutic stimulation parameters, the processing circuitry is configured to: determine a summed CMAP signal based on a summation of the first CMAP signal and the second CMAP signal; compare the summed CMAP signal to the combined CMAP signal; and determine, based on the comparison, the one or more therapeutic stimulation parameters.

Example 14. A method of obstructive sleep apnea (OSA) treatment, the method comprising: causing, with processing circuitry, therapy delivery circuitry to output one or more electrical stimulation signals to a tongue of a patient via a first electrode configured to be implanted within the tongue; receiving, with the processing circuitry, information indicative of one or more compound muscle action potential (CMAP) signals from a sensing circuitry configured to sense the one or more CMAP signals via a second electrode configured to be implanted within the tongue, wherein the one or more CMAP signals are generated in response to the delivery of the one or more electrical stimulation signals; determining, with the processing circuitry and based on the one or more CMAP signals, one or more therapeutic stimulation parameters for the OSA treatment; and causing, with the processing circuitry, the therapy delivery circuitry to deliver therapeutic electrical stimulation signals according to at least the determined one or more therapeutic stimulation parameters.

Example 15. The method of example 14, wherein causing the therapy delivery circuitry to output the one or more electrical stimulation signals comprises causing the therapy delivery circuitry to output a plurality of electrical stimulation signals having different energy, wherein receiving information indicative of the one or more CMAP signals comprises receiving information indicative of each of a plurality of CMAP signals each generated in response to a respective one of the plurality of electrical stimulation signals, the method further comprising comparing two or more of the plurality of CMAP signals to each other, and determining the one or more therapeutic stimulation parameters based on the one or more CMAP signals for OSA treatment comprises determining, based on the comparison, the one or more therapeutic stimulation parameters.

Example 16. The method of example 15, wherein determining, based on the comparison, the one or more therapeutic stimulation parameters comprises: determining for which one of the two or more of the plurality of CMAP signals there is a change relative to another one of the two or more of the plurality of CMAP signals; determining an electrical stimulation signal of the plurality of electrical stimulation parameters that generated the determined one of the plurality of CMAP signals; determining one or more stimulation parameters for the determined electrical stimulation signal; and determining the one or more therapeutic stimulation parameters based on the determined one or more stimulation parameters.

Example 17. The method of example 16, wherein the change includes a change in one or more of an amplitude between the two or more of the plurality of CMAP signals, a shape between the two or more of the plurality of CMAP signals, and whether there is a change in a variance between the two or more of the plurality of CMAP signals.

Example 18. The method of any of examples 14-17, wherein the one or more CMAP signals comprise a first set of one or more CMAP signals, the method further comprising, subsequent to the delivery of the therapeutic electrical stimulation signals:
receiving information indicative of a second set of CMAP signals generated in response to the delivery of the therapeutic electrical stimulation signals; comparing two or more CMAP signals of the second set of CMAP signals to each other; determining that the tongue is experiencing fatigue based on the comparison; and controlling the therapy delivery circuitry based on the determination that the tongue is experiencing fatigue.

Example 19. The method of any of examples 14-18, wherein the one or more CMAP signals includes an artifact portion and a non-artifact portion, wherein determining the one or more therapeutic stimulation parameters comprises determining the one or more therapeutic stimulation parameters based on: both the artifact portion and the non-artifact portion of the one or more CMAP signals; the non-artifact portion of the one or more CMAP signals, and not the artifact portion; or the artifact portion of the one or more CMAP signals, and not the non-artifact portion.

Example 20. A computer-readable storage medium storing instructions thereon that when executed cause one or more processors to: cause therapy delivery circuitry to output one or more electrical stimulation signals to a tongue of a patient via a first electrode configured to be implanted within the tongue; receive information indicative of one or more compound muscle action potential (CMAP) signals from a sensing circuitry configured to sense the one or more CMAP signals via a second electrode configured to be implanted within the tongue, wherein the one or more CMAP signals are generated in response to the delivery of the one or more electrical stimulation signals; determine, based on the one or more CMAP signals, one or more therapeutic stimulation parameters for the OSA treatment; and cause the therapy delivery circuitry to deliver therapeutic electrical stimulation signals according to at least the determined one or more therapeutic stimulation parameters.

Example 21. A medical system for obstructive sleep apnea (OSA) treatment, the system comprising: means for causing therapy delivery circuitry to output one or more electrical stimulation signals to a tongue of a patient via a first electrode configured to be implanted within the tongue; means for receiving information indicative of one or more compound muscle action potential (CMAP) signals from a sensing circuitry configured to sense the one or more CMAP signals via a second electrode configured to be implanted within the tongue, wherein the one or more CMAP signals are generated in response to the delivery of the one or more electrical stimulation signals; means for determining, based on the one or more CMAP signals, one or more therapeutic stimulation parameters for the OSA treatment; and means for causing the therapy delivery circuitry to deliver therapeutic electrical stimulation signals according to at least the determined one or more therapeutic stimulation parameters.

Example 22. The system of example 21 further comprising means for performing the example of any of methods 14-19.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A medical system for obstructive sleep apnea (OSA) treatment, the system comprising:
    therapy delivery circuitry configured to output one or more electrical stimulation signals to a tongue of a patient via a first electrode configured to be implantable within the tongue;
    sensing circuitry configured to sense a plurality of compound muscle action potential (CMAP) signals via one or more second electrodes configured to be implantable within the tongue, wherein the plurality of CMAP signals are generated in response to the delivery of the one or more electrical stimulation signals; and
    processing circuitry configured to:
        cause the therapy delivery circuitry to output the one or more electrical stimulation signals to the tongue;
        determine, based on the plurality of CMAP signals, one or more therapeutic stimulation parameters for the OSA treatment, wherein to determine the one or more therapeutic stimulation parameters, the processing circuitry is configured to:
            determine a summed CMAP signal based on a summation of a first CMAP signal of the plurality of CMAP signals and a second CMAP signal of the plurality of CMAP signals, the first CMAP signal being evoked on a first side of the tongue, and the second CMAP signal being evoked on one of a second side of the tongue or on the first side of the tongue;
            compare the summed CMAP signal to a combined CMAP signal, the combined CMAP signal being simultaneously evoked on both the first side and the second side or evoked on the first side with stimulation from a plurality of electrodes on the first side; and
            determine, based on the comparison, the one or more therapeutic stimulation parameters; and
        cause the therapy delivery circuitry to deliver therapeutic electrical stimulation signals according to at least the determined one or more therapeutic stimulation parameters.

2. The medical system of claim 1, further comprising an implantable medical device (IMD), wherein the IMD includes the therapy delivery circuitry, the sensing circuitry, and at least a portion of the processing circuitry.

3. The medical system of claim 1, further comprising an implantable medical device (IMD) and an external programmer, wherein the IMD includes the therapy delivery circuitry and the sensing circuitry, and wherein the external programmer includes at least a portion of the processing circuitry.

4. The medical system of claim 1,
wherein to cause the therapy delivery circuitry to output the one or more electrical stimulation signals, the processing circuitry is configured to cause the therapy delivery circuitry to output a plurality of electrical stimulation signals having different energy.

5. The system of claim 1, wherein to determine, based on the comparison, the one or more therapeutic stimulation parameters, the processing circuitry is configured to:
determine whether there is cross-innervation based on the comparison; and
determine the one or more therapeutic stimulation parameters based on whether there is cross-innervation.

6. The system of claim 1, wherein the plurality of CMAP signals comprise a first set of CMAP signals, and wherein, subsequent to the delivery of the therapeutic electrical stimulation signals, the processing circuitry is configured to:
compare two or more CMAP signals of a second set of CMAP signals to each other, the second set of CMAP signals being generated in response to the delivery of the therapeutic electrical stimulation signals;
determine that the tongue is experiencing fatigue based on the comparison of the two or more CMAP signals of the second set of CMAP signals; and
control the therapy delivery circuitry based on the determination that the tongue is experiencing fatigue.

7. The system of claim 6, wherein to control the therapy delivery circuitry, the processing circuitry is configured to:
update one or more of the one or more stimulation parameters to generate updated one or more stimulation parameters based on the comparison of the two or more CMAP signals of the second set of CMAP signals; and
cause the therapy delivery circuitry to deliver updated therapeutic electrical stimulation signals based on the updated one or more stimulation parameters.

8. The system of claim 6, wherein to control the therapy delivery circuitry, the processing circuitry is configured to:
cause the therapy delivery circuitry to cease delivery of the therapeutic electrical stimulation signals.

9. The system of claim 6, wherein to compare the two or more CMAP signals of the second set of CMAP signals to each other, the processing circuitry is configured to determine whether there is a change in one or more of an amplitude between the two or more of the second set of CMAP signals, a shape between the two or more of the second set of CMAP signals, and whether there is a change in a variance between the two or more of the second set of CMAP signals.

10. The system of claim 1, further comprising an accelerometer configured to generate information, wherein the processing circuitry is configured to receive the information, and determine whether there is a change in patient posture based on the received information, and wherein the processing circuitry is configured to, in response to the determination that there is the change in patient posture:
cause the therapy delivery circuitry to output the one or more electrical stimulation signals to the tongue; and
determine the one or more therapeutic stimulation parameters based on the ene or more plurality of CMAP signals for the OSA treatment.

11. The system of claim 1, wherein the each of the plurality of CMAP signals includes an artifact portion and a non-artifact portion, wherein to determine the one or more therapeutic stimulation parameters, the processing circuitry is configured to determine the one or more therapeutic stimulation parameters based on:
both the artifact portion and the non-artifact portion;
the non-artifact portion, and not the artifact portion; or
the artifact portion, and not the non-artifact portion.

12. A method of obstructive sleep apnea (OSA) treatment, the method comprising:
outputting, with therapy delivery circuitry, one or more electrical stimulation signals to a tongue of a patient via a first electrode configured to be implanted within the tongue;
sensing, with sensing circuitry, a plurality of compound muscle action potential (CMAP) signals via one or more second electrodes configured to be implanted within the tongue, wherein the plurality of CMAP signals are generated in response to the delivery of the one or more electrical stimulation signals;
determining, with processing circuitry and based on the plurality of CMAP signals, one or more therapeutic stimulation parameters for the OSA treatment, wherein determining the one or more therapeutic stimulation parameters comprises:
determining a summed CMAP signal based on a summation of a first CMAP signal of the plurality of CMAP signals and a second CMAP signal of the plurality of CMAP signals, the first CMAP signal being evoked on a first side of the tongue, and the second CMAP signal being evoked on one of a second side of the tongue or on the first side of the tongue;
comparing the summed CMAP signal to a combined CMAP signal, the combined CMAP signal being simultaneously evoked on both the first side and the second side or evoked on the first side with stimulation from a plurality of electrodes on the first side; and
determining, based on the comparison, the one or more therapeutic stimulation parameters; and
causing, with the processing circuitry, the therapy delivery circuitry to deliver therapeutic electrical stimulation signals according to at least the determined one or more therapeutic stimulation parameters.

13. The method of claim 12,
wherein causing the therapy delivery circuitry to output the one or more electrical stimulation signals comprises causing the therapy delivery circuitry to output a plurality of electrical stimulation signals having different energy.

14. The method of claim 12, wherein determining, based on the comparison, the one or more therapeutic stimulation parameters comprises:
determining whether there is cross-innervation based on the comparison; and
determining the one or more therapeutic stimulation parameters based on whether there is cross-innervation.

15. The method of claim 12, wherein the plurality of CMAP signals comprise a first set of CMAP signals, the method further comprising, subsequent to the delivery of the therapeutic electrical stimulation signals:
comparing two or more CMAP signals of a second set of CMAP signals to each other, the second set of CMAP signals being generated in response to the delivery of the therapeutic electrical stimulation signals;

determining that the tongue is experiencing fatigue based on the comparison of the two or more CMAP signals of the second set of CMAP signals; and controlling the therapy delivery circuitry based on the determination that the tongue is experiencing fatigue.

16. The method of claim 12, wherein the each of the plurality of CMAP signals includes an artifact portion and a non-artifact portion, wherein determining the one or more therapeutic stimulation parameters comprises determining the one or more therapeutic stimulation parameters based on:

both the artifact portion and the non-artifact portion;
the non-artifact portion, and not the artifact portion; or
the artifact portion, and not the non-artifact portion.

* * * * *